(12) United States Patent
Neri et al.

(10) Patent No.: US 8,404,814 B2
(45) Date of Patent: Mar. 26, 2013

(54) ANTI-EDB ANTIBODY-TARGETED IL-10 CYTOKINE FOR THERAPY OF RHEUMATOID ARTHRITIS

(75) Inventors: Dario Neri, Buchs (CH); Manuela Kaspar, Brugg (CH); Eveline Trachsel, Baden (CH)

(73) Assignee: Philogen SpA, Siena (IT)

( * ) Notice: Subject to any disclaimer, the term of this patent is extended or adjusted under 35 U.S.C. 154(b) by 496 days.

(21) Appl. No.: 12/227,060

(22) PCT Filed: May 8, 2007

(86) PCT No.: PCT/EP2007/004044
§ 371 (c)(1),
(2), (4) Date: Jun. 1, 2011

(87) PCT Pub. No.: WO2007/128563
PCT Pub. Date: Nov. 15, 2007

(65) Prior Publication Data
US 2011/0256091 A1 Oct. 20, 2011

(30) Foreign Application Priority Data
May 8, 2006 (EP) .................................... 06009456

(51) Int. Cl.
C07K 19/00 (2006.01)
C07K 14/54 (2006.01)
C12N 15/24 (2006.01)
A61K 39/00 (2006.01)
A61K 38/20 (2006.01)
A61P 19/02 (2006.01)
A61P 29/00 (2006.01)
C12N 15/62 (2006.01)

(52) U.S. Cl. ................. 530/387.3; 435/69.7; 424/192.1; 514/16.6; 514/21.2; 530/399; 930/141; 536/23.4

(58) Field of Classification Search ........................ None
See application file for complete search history.

(56) References Cited

U.S. PATENT DOCUMENTS
2011/0256091 A1* 10/2011 Neri et al. .................... 424/85.2

OTHER PUBLICATIONS
Trachsel et al (2007. Arthritis Research & Therapy. 9:R9; 9 pages total).*
Schwager et al (2009. 11: R145; 15 pages total).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*

*Primary Examiner* — Zachary Howard
(74) *Attorney, Agent, or Firm* — Nath, Goldberg & Meyer; Tanya E. Harkins

(57) ABSTRACT

The present invention relates to fusion proteins comprising an antibody, functional fragment or functional derivative thereof having specific binding affinity to either the extracellular domain of oncofetal fibronectin (ED-B) or at least one of the extracellular domains of oncofetal tenascin fused to a cytokine selected from the group consisting of IL-10, IL15, IL-24 and GM-CSF, functional fragments and functional derivatives thereof. The invention is also directed to the use of at least one of said fusion proteins for the manufacture of a medicament. In particular, the invention concerns the use of said medicament for the treatment of tumors or chronic inflammatory diseases such as atherosclerosis, arthritis and psoriasis.

12 Claims, 5 Drawing Sheets

SEQUENCE LISTING

<160> NUMBER OF SEQ ID NOS: 19

<210> SEQ ID NO 1
<211> LENGTH: 178
<212> TYPE: PRT
<213> ORGANISM: Homo sapiens

<400> SEQUENCE: 1

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 2
<211> LENGTH: 114
<212> TYPE: PRT
<213> ORGANISM: Homo sapiens

<400> SEQUENCE: 2

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
```

```
                65                  70                  75                  80
Thr Glu Ser Gly Cys Lys Glu Cys Glu Leu Glu Glu Lys Asn Ile
                    85                  90                  95

Lys Glu Phe Leu Gln Ser Phe Val His Ile Val Gln Met Phe Ile Asn
                100                 105                 110

Thr Ser

<210> SEQ ID NO 3
<211> LENGTH: 158
<212> TYPE: PRT
<213> ORGANISM: Homo sapiens

<400> SEQUENCE: 3

Ala Gln Gly Gln Glu Phe His Phe Gly Pro Cys Gln Val Lys Gly Val
1               5                   10                  15

Val Pro Gln Lys Leu Trp Glu Ala Phe Trp Ala Val Lys Asp Thr Met
                20                  25                  30

Gln Ala Gln Asp Asn Ile Thr Ser Ala Arg Leu Leu Gln Gln Glu Val
            35                  40                  45

Leu Gln Asn Val Ser Asp Ala Glu Ser Cys Tyr Leu Val His Thr Leu
        50                  55                  60

Leu Glu Phe Tyr Leu Lys Thr Val Phe Lys Asn Tyr His Asn Arg Thr
65                  70                  75                  80

Val Glu Val Arg Thr Leu Lys Ser Phe Ser Thr Leu Ala Asn Asn Phe
                85                  90                  95

Val Leu Ile Val Ser Gln Leu Gln Pro Ser Gln Glu Asn Glu Met Phe
                100                 105                 110

Ser Ile Arg Asp Ser Ala His Arg Arg Phe Leu Leu Phe Arg Arg Ala
            115                 120                 125

Phe Lys Gln Leu Asp Val Glu Ala Ala Leu Thr Lys Ala Leu Gly Glu
        130                 135                 140

Val Asp Ile Leu Leu Thr Trp Met Gln Lys Phe Tyr Lys Leu
145                 150                 155

<210> SEQ ID NO 4
<211> LENGTH: 127
<212> TYPE: PRT
<213> ORGANISM: Homo sapiens

<400> SEQUENCE: 4

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125
```

<210> SEQ ID NO 5
<211> LENGTH: 124
<212> TYPE: PRT
<213> ORGANISM: Mus musculus

<400> SEQUENCE: 5

```
Ala Pro Thr Arg Ser Pro Ile Thr Val Thr Arg Pro Trp Lys His Val
 1               5                  10                  15

Glu Ala Ile Lys Glu Ala Leu Asn Leu Leu Asp Asp Met Pro Val Thr
             20                  25                  30

Leu Asn Glu Glu Val Glu Val Val Ser Asn Glu Phe Ser Phe Lys Lys
         35                  40                  45

Leu Thr Cys Val Gln Thr Arg Leu Lys Ile Phe Glu Gln Gly Leu Arg
     50                  55                  60

Gly Asn Phe Thr Lys Leu Lys Gly Ala Leu Asn Met Thr Ala Ser Tyr
 65                  70                  75                  80

Tyr Gln Thr Tyr Cys Pro Pro Thr Pro Glu Thr Asp Cys Glu Thr Gln
                 85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Val Gln Lys
        115                 120
```

<210> SEQ ID NO 6
<211> LENGTH: 238
<212> TYPE: PRT
<213> ORGANISM: Artificial Sequence
<220> FEATURE:
<223> OTHER INFORMATION: Antibody fragment L19 (long)

<400> SEQUENCE: 6

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
             20                  25                  30

Ser Met Ser Trp Val Arg Gln Ala Pro Gly Lys Gly Leu Glu Trp Val
         35                  40                  45

Ser Ser Ile Ser Gly Ser Ser Gly Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ala Ser
        115                 120                 125

Thr Gly Glu Ile Val Leu Thr Gln Ser Pro Gly Thr Leu Ser Leu Ser
    130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
                165                 170                 175

Leu Leu Ile Tyr Tyr Ala Ser Ser Arg Ala Thr Gly Ile Pro Asp Arg
            180                 185                 190

Phe Ser Gly Ser Gly Ser Gly Thr Asp Phe Thr Leu Thr Ile Ser Arg
        195                 200                 205
```

```
Leu Glu Pro Glu Asp Phe Ala Val Tyr Tyr Cys Gln Gln Thr Gly Arg
    210                 215                 220

Ile Pro Pro Thr Phe Gly Gln Gly Thr Lys Val Glu Ile Lys
225                 230                 235

<210> SEQ ID NO 7
<211> LENGTH: 229
<212> TYPE: PRT
<213> ORGANISM: Artificial Sequence
<220> FEATURE:
<223> OTHER INFORMATION: Antibody fragment L19 (short)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Ser Gly Gly Glu Ile Val Leu Thr Gln Ser
        115                 120                 125

Pro Gly Thr Leu Ser Leu Ser Pro Gly Glu Arg Ala Thr Leu Ser Cys
    130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
        195                 200                 205

Tyr Cys Gln Gln Thr Gly Arg Ile Pro Pro Thr Phe Gly Gln Gly Thr
    210                 215                 220

Lys Val Glu Ile Lys
225

<210> SEQ ID NO 8
<211> LENGTH: 239
<212> TYPE: PRT
<213> ORGANISM: Artificial Sequence
<220> FEATURE:
<223> OTHER INFORMATION: Antibody fragment F16 (long)

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Ala Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala His Asn Ala Phe Asp Tyr Trp Gly Gln Gly Thr Leu Val
                100                 105                 110

Thr Val Ser Arg Gly Gly Gly Ser Gly Gly Gly Ser Gly Gly
                115                 120                 125

Gly Gly Ser Ser Glu Leu Thr Gln Asp Pro Ala Val Ser Val Ala Leu
130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
                180                 185                 190

Gly Ser Ser Ser Gly Asn Thr Ala Ser Leu Thr Ile Thr Gly Ala Gln
                195                 200                 205

Ala Glu Asp Glu Ala Asp Tyr Tyr Cys Asn Ser Val Tyr Thr Met
210                 215                 220

Pro Pro Val Val Phe Gly Gly Gly Thr Lys Leu Thr Val Leu Gly
225                 230                 235

<210> SEQ ID NO 9
<211> LENGTH: 230
<212> TYPE: PRT
<213> ORGANISM: Artificial Sequence
<220> FEATURE:
<223> OTHER INFORMATION: Antibody fragment F16 (short)

<400> SEQUENCE: 9

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                 20                  25                  30

Gly Ala Ser Trp Val Arg Gln Ala Pro Gly Lys Gly Leu Glu Trp Val
                 35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala His Asn Ala Phe Asp Tyr Trp Gly Gln Gly Thr Leu Val
                100                 105                 110

Thr Val Ser Arg Gly Ser Ser Gly Gly Ser Ser Glu Leu Thr Gln Asp
                115                 120                 125

Pro Ala Val Ser Val Ala Leu Gly Gln Thr Val Arg Ile Thr Cys Gln
130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175
```

```
Gly Ile Pro Asp Arg Phe Ser Gly Ser Ser Gly Asn Thr Ala Ser
            180                 185                 190

Leu Thr Ile Thr Gly Ala Gln Ala Glu Asp Glu Ala Asp Tyr Tyr Cys
        195                 200                 205

Asn Ser Ser Val Tyr Thr Met Pro Pro Val Val Phe Gly Gly Gly Thr
210                 215                 220

Lys Leu Thr Val Leu Gly
225                 230

<210> SEQ ID NO 10
<211> LENGTH: 239
<212> TYPE: PRT
<213> ORGANISM: Artificial Sequence
<220> FEATURE:
<223> OTHER INFORMATION: Antibody fragment F16(A34M) (long)

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Val Tyr Thr Met
    210                 215                 220

Pro Pro Val Val Phe Gly Gly Gly Thr Lys Leu Thr Val Leu Gly
225                 230                 235

<210> SEQ ID NO 11
<211> LENGTH: 230
<212> TYPE: PRT
<213> ORGANISM: Artificial Sequence
<220> FEATURE:
<223> OTHER INFORMATION: Antibody fragment F16(A34M) (short)

<400> SEQUENCE: 11

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Ser Ser Gly Ser Ser Glu Leu Thr Gln Asp
        115                 120                 125

Pro Ala Val Ser Val Ala Leu Gly Gln Thr Val Arg Ile Thr Cys Gln
    130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
            165                 170                 175

Gly Ile Pro Asp Arg Phe Ser Gly Ser Ser Ser Gly Asn Thr Ala Ser
        180                 185                 190

Leu Thr Ile Thr Gly Ala Gln Ala Glu Asp Glu Ala Asp Tyr Tyr Cys
    195                 200                 205

Asn Ser Ser Val Tyr Thr Met Pro Pro Val Val Phe Gly Gly Gly Thr
210                 215                 220

Lys Leu Thr Val Leu Gly
225                 230

<210> SEQ ID NO 12
<211> LENGTH: 241
<212> TYPE: PRT
<213> ORGANISM: Artificial Sequence
<220> FEATURE:
<223> OTHER INFORMATION: Antibody fragment G11(long)

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Arg Met Gly Trp Val Arg Gln Ala Pro Gly Lys Gly Leu Glu Trp Val
        35                  40                  45

Ser Ala Ile Asn Glu Glu Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Arg Gly Gly Gly Ser Gly Gly Gly Ser
        115                 120                 125

Gly Gly Gly Gly Ser Ser Glu Leu Thr Gln Asp Pro Ala Val Ser Val
130                 135                 140

Ala Leu Gly Gln Thr Val Arg Ile Thr Cys Gln Gly Asp Ser Leu Arg
```

-continued

```
                145                 150                 155                 160
Leu Tyr Tyr Ala Ser Trp Tyr Gln Gln Lys Pro Gly Gln Ala Pro Val
            165                 170                 175

Leu Val Ile Tyr Gly Lys Asn Asn Arg Pro Ser Gly Ile Pro Asp Arg
        180                 185                 190

Phe Ser Gly Ser Ser Gly Asn Thr Ala Ser Leu Thr Ile Thr Gly
        195                 200                 205

Ala Gln Ala Glu Asp Glu Ala Asp Tyr Tyr Cys Asn Ser His Gly
    210                 215                 220

Pro Arg Arg Pro Val Val Phe Gly Gly Gly Thr Lys Leu Thr Val Leu
225                 230                 235                 240

Gly

<210> SEQ ID NO 13
<211> LENGTH: 232
<212> TYPE: PRT
<213> ORGANISM: Artificial Sequence
<220> FEATURE:
<223> OTHER INFORMATION: Antibody fragment G11(short)

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Arg Met Gly Trp Val Arg Gln Ala Pro Gly Lys Gly Leu Glu Trp Val
        35                  40                  45

Ser Ala Ile Asn Glu Glu Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Arg Gly Ser Gly Gly Ser Ser Glu Leu Thr
        115                 120                 125

Gln Asp Pro Ala Val Ser Val Ala Leu Gly Gln Thr Val Arg Ile Thr
    130                 135                 140

Cys Gln Gly Asp Ser Leu Arg Leu Tyr Tyr Ala Ser Trp Tyr Gln Gln
145                 150                 155                 160

Lys Pro Gly Gln Ala Pro Val Leu Val Ile Tyr Gly Lys Asn Asn Arg
                165                 170                 175

Pro Ser Gly Ile Pro Asp Arg Phe Ser Gly Ser Ser Ser Gly Asn Thr
            180                 185                 190

Ala Ser Leu Thr Ile Thr Gly Ala Gln Ala Glu Asp Glu Ala Asp Tyr
        195                 200                 205

Tyr Cys Asn Ser Ser His Gly Pro Arg Arg Pro Val Val Phe Gly Gly
    210                 215                 220

Gly Thr Lys Leu Thr Val Leu Gly
225                 230

<210> SEQ ID NO 14
<211> LENGTH: 413
<212> TYPE: PRT
<213> ORGANISM: Artificial Sequence
<220> FEATURE:
```

-continued

<223> OTHER INFORMATION: Fusion protein of antibody fragment L19(long) and cytokine huIL-10

<400> SEQUENCE: 14

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Gly Gly Ser Gly Gly Ser Gly Ala Ser
        115                 120                 125

Thr Gly Glu Ile Val Leu Thr Gln Ser Pro Gly Thr Leu Ser Leu Ser
    130                 135                 140

Pro Gly Glu Arg Ala Thr Leu Ser Cys Arg Ala Ser Gln Ser Val Ser
145                 150                 155                 160

Ser Ser Tyr Leu Ala Trp Tyr Gln Gln Lys Pro Gly Gln Ala Pro Arg
                165                 170                 175

Leu Leu Ile Tyr Tyr Ala Ser Ser Arg Ala Thr Gly Ile Pro Asp Arg
            180                 185                 190

Phe Ser Gly Ser Gly Ser Gly Thr Asp Phe Thr Leu Thr Ile Ser Arg
        195                 200                 205

Leu Glu Pro Glu Asp Phe Ala Val Tyr Tyr Cys Gln Gln Thr Gly Arg
    210                 215                 220

Ile Pro Pro Thr Phe Gly Gln Gly Thr Lys Val Glu Ile Lys Ser Ser
225                 230                 235                 240

Ser Ser Gly Ser Ser Ser Gly Ser Ser Ser Gly Ser Pro Gly
                245                 250                 255

Gln Gly Thr Gln Ser Glu Asn Ser Cys Thr His Phe Pro Gly Asn Leu
            260                 265                 270

Pro Asn Met Leu Arg Asp Leu Arg Asp Ala Phe Ser Arg Val Lys Thr
        275                 280                 285

Phe Phe Gln Met Lys Asp Gln Leu Asp Asn Leu Leu Leu Lys Glu Ser
    290                 295                 300

Leu Leu Glu Asp Phe Lys Gly Tyr Leu Gly Cys Gln Ala Leu Ser Glu
305                 310                 315                 320

Met Ile Gln Phe Tyr Leu Glu Glu Val Met Pro Gln Ala Glu Asn Gln
                325                 330                 335

Asp Pro Asp Ile Lys Ala His Val Asn Ser Leu Gly Glu Asn Leu Lys
            340                 345                 350

Thr Leu Arg Leu Arg Leu Arg Arg Cys His Arg Phe Leu Pro Cys Glu
        355                 360                 365

Asn Lys Ser Lys Ala Val Glu Gln Val Lys Asn Ala Phe Asn Lys Leu
    370                 375                 380

Gln Glu Lys Gly Ile Tyr Lys Ala Met Ser Glu Phe Asp Ile Phe Ile
385                 390                 395                 400
```

Asn Tyr Ile Glu Ala Tyr Met Thr Met Lys Ile Arg Asn
            405                 410

<210> SEQ ID NO 15
<211> LENGTH: 358
<212> TYPE: PRT
<213> ORGANISM: Artificial Sequence
<220> FEATURE:
<223> OTHER INFORMATION: Fusion protein of antibody fragment L19(short)
      and cytokine huIL15

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Ser Ser Gly Gly Glu Ile Val Leu Thr Gln Ser
        115                 120                 125

Pro Gly Thr Leu Ser Leu Ser Pro Gly Glu Arg Ala Thr Leu Ser Cys
    130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
        195                 200                 205

Tyr Cys Gln Gln Thr Gly Arg Ile Pro Pro Thr Phe Gly Gln Gly Thr
    210                 215                 220

Lys Val Glu Ile Lys Ser Ser Ser Gly Ser Ser Ser Ser Gly Ser
225                 230                 235                 240

Ser Ser Ser Gly Asn Trp Val Asn Val Ile Ser Asp Leu Lys Lys Ile
                245                 250                 255

Glu Asp Leu Ile Gln Ser Met His Ile Asp Ala Thr Leu Tyr Thr Glu
            260                 265                 270

Ser Asp Val His Pro Ser Cys Lys Val Thr Ala Met Lys Cys Phe Leu
        275                 280                 285

Leu Glu Leu Gln Val Ile Ser Leu Glu Ser Gly Asp Ala Ser Ile His
    290                 295                 300

Asp Thr Val Glu Asn Leu Ile Ile Leu Ala Asn Asn Ser Leu Ser Ser
305                 310                 315                 320

Asn Gly Asn Val Thr Glu Ser Gly Cys Lys Glu Cys Glu Glu Leu Glu
                325                 330                 335

Glu Lys Asn Ile Lys Glu Phe Leu Gln Ser Phe Val His Ile Val Gln
            340                 345                 350

```
Met Phe Ile Asn Thr Ser
            355
```

<210> SEQ ID NO 16
<211> LENGTH: 358
<212> TYPE: PRT
<213> ORGANISM: Artificial Sequence
<220> FEATURE:
<223> OTHER INFORMATION: Fusion protein of cytokine huIL15 and antibody
      fragment L19(short)

<400> SEQUENCE: 16

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Ser Ser Ser Gly Ser Ser Ser Gly Ser Ser Ser Ser
        115                 120                 125

Gly Glu Val Gln Leu Leu Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

Phe Ser Met Ser Trp Val Arg Gln Ala Pro Gly Lys Gly Leu Glu Trp
                165                 170                 175

Val Ser Ser Ile Ser Gly Ser Ser Gly Thr Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Lys Pro Phe Pro Tyr Phe Asp Tyr Trp Gly Gln Gly Thr Leu
225                 230                 235                 240

Val Thr Val Ser Ser Gly Ser Ser Gly Gly Glu Ile Val Leu Thr Gln
                245                 250                 255

Ser Pro Gly Thr Leu Ser Leu Ser Pro Gly Glu Arg Ala Thr Leu Ser
            260                 265                 270

Cys Arg Ala Ser Gln Ser Val Ser Ser Ser Phe Leu Ala Trp Tyr Gln
        275                 280                 285

Gln Lys Pro Gly Gln Ala Pro Arg Leu Leu Ile Tyr Tyr Ala Ser Ser
    290                 295                 300

Arg Ala Thr Gly Ile Pro Asp Arg Phe Ser Gly Ser Gly Ser Gly Thr
305                 310                 315                 320

Asp Phe Thr Leu Thr Ile Ser Arg Leu Glu Pro Glu Asp Phe Ala Val
                325                 330                 335

Tyr Tyr Cys Gln Gln Thr Gly Arg Ile Pro Thr Pro Phe Gly Gln Gly
            340                 345                 350
```

Thr Lys Val Glu Ile Lys
        355

<210> SEQ ID NO 17
<211> LENGTH: 402
<212> TYPE: PRT
<213> ORGANISM: Artificial Sequence
<220> FEATURE:
<223> OTHER INFORMATION: Fusion protein of cytokine huIL24 and antibody
      fragment L19(short)

<400> SEQUENCE: 17

Ala Gln Gly Gln Glu Phe His Phe Gly Pro Cys Gln Val Lys Gly Val
1               5                   10                  15

Val Pro Gln Lys Leu Trp Glu Ala Phe Trp Ala Val Lys Asp Thr Met
            20                  25                  30

Gln Ala Gln Asp Asn Ile Thr Ser Ala Arg Leu Leu Gln Gln Glu Val
        35                  40                  45

Leu Gln Asn Val Ser Asp Ala Glu Ser Cys Tyr Leu Val His Thr Leu
    50                  55                  60

Leu Glu Phe Tyr Leu Lys Thr Val Phe Lys Asn Tyr His Asn Arg Thr
65                  70                  75                  80

Val Glu Val Arg Thr Leu Lys Ser Phe Ser Thr Leu Ala Asn Asn Phe
                85                  90                  95

Val Leu Ile Val Ser Gln Leu Gln Pro Ser Gln Glu Asn Glu Met Phe
            100                 105                 110

Ser Ile Arg Asp Ser Ala His Arg Arg Phe Leu Leu Phe Arg Arg Ala
        115                 120                 125

Phe Lys Gln Leu Asp Val Glu Ala Ala Leu Thr Lys Ala Leu Gly Glu
    130                 135                 140

Val Asp Ile Leu Leu Thr Trp Met Gln Lys Phe Tyr Lys Leu Ser Ser
145                 150                 155                 160

Ser Ser Gly Ser Ser Ser Gly Ser Ser Ser Gly Glu Val Gln
                165                 170                 175

Leu Leu Glu Ser Gly Gly Gly Leu Val Gln Pro Gly Gly Ser Leu Arg
            180                 185                 190

Leu Ser Cys Ala Ala Ser Gly Phe Thr Phe Ser Ser Phe Ser Met Ser
        195                 200                 205

Trp Val Arg Gln Ala Pro Gly Lys Gly Leu Glu Trp Val Ser Ser Ile
    210                 215                 220

Ser Gly Ser Ser Gly Thr Thr Tyr Tyr Ala Asp Ser Val Lys Gly Arg
225                 230                 235                 240

Phe Thr Ile Ser Arg Asp Asn Ser Lys Asn Thr Leu Tyr Leu Gln Met
                245                 250                 255

Asn Ser Leu Arg Ala Glu Asp Thr Ala Val Tyr Tyr Cys Ala Lys Pro
            260                 265                 270

Phe Pro Tyr Phe Asp Tyr Trp Gly Gln Gly Thr Leu Val Thr Val Ser
        275                 280                 285

Ser Gly Ser Ser Gly Gly Glu Ile Val Leu Thr Gln Ser Pro Gly Thr
    290                 295                 300

Leu Ser Leu Ser Pro Gly Glu Arg Ala Thr Leu Ser Cys Arg Ala Ser
305                 310                 315                 320

Gln Ser Val Ser Ser Ser Phe Leu Ala Trp Tyr Gln Gln Lys Pro Gly
                325                 330                 335

Gln Ala Pro Arg Leu Leu Ile Tyr Tyr Ala Ser Ser Arg Ala Thr Gly
            340                 345                 350

```
Ile Pro Asp Arg Phe Ser Gly Ser Gly Ser Gly Thr Asp Phe Thr Leu
        355                 360                 365

Thr Ile Ser Arg Leu Glu Pro Glu Asp Phe Ala Val Tyr Tyr Cys Gln
    370                 375                 380

Gln Thr Gly Arg Ile Pro Pro Thr Phe Gly Gln Gly Thr Lys Val Glu
385                 390                 395                 400

Ile Lys

<210> SEQ ID NO 18
<211> LENGTH: 371
<212> TYPE: PRT
<213> ORGANISM: Artificial Sequence
<220> FEATURE:
<223> OTHER INFORMATION: Fusion Protein of antibody fragment L19(short)
      and cytokine huGM-CSF

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Ser Ser Gly Gly Glu Ile Val Leu Thr Gln Ser
        115                 120                 125

Pro Gly Thr Leu Ser Leu Ser Pro Gly Glu Arg Ala Thr Leu Ser Cys
    130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
        195                 200                 205

Tyr Cys Gln Gln Thr Gly Arg Ile Pro Pro Thr Phe Gly Gln Gly Thr
    210                 215                 220

Lys Val Glu Ile Lys Ser Ser Ser Ser Gly Ser Ser Ser Ser Gly Ser
225                 230                 235                 240

Ser Ser Ser Gly Ala Pro Ala Arg Ser Pro Ser Pro Ser Thr Gln Pro
                245                 250                 255

Trp Glu His Val Asn Ala Ile Gln Glu Ala Arg Arg Leu Leu Asn Leu
            260                 265                 270

Ser Arg Asp Thr Ala Ala Glu Met Asn Glu Thr Val Glu Val Ile Ser
        275                 280                 285

Glu Met Phe Asp Leu Gln Glu Pro Thr Cys Leu Gln Thr Arg Leu Glu
    290                 295                 300

Leu Tyr Lys Gln Gly Leu Arg Gly Ser Leu Thr Lys Leu Lys Gly Pro
```

```
                 305                 310                 315                 320
Leu Thr Met Met Ala Ser His Tyr Lys Gln His Cys Pro Pro Thr Pro
                325                 330                 335

Glu Thr Ser Cys Ala Thr Gln Ile Ile Thr Phe Glu Ser Phe Lys Glu
            340                 345                 350

Asn Leu Lys Asp Phe Leu Leu Val Ile Pro Phe Asp Cys Trp Glu Pro
        355                 360                 365

Val Gln Glu
    370

<210> SEQ ID NO 19
<211> LENGTH: 368
<212> TYPE: PRT
<213> ORGANISM: Artificial Sequence
<220> FEATURE:
<223> OTHER INFORMATION: Fusion protein of antibody fragment L19(short)
      and cytokine murine GM-CSF

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Ser Ser Gly Gly Glu Ile Val Leu Thr Gln Ser
        115                 120                 125

Pro Gly Thr Leu Ser Leu Ser Pro Gly Glu Arg Ala Thr Leu Ser Cys
    130                 135                 140

Arg Ala Ser Gln Ser Val Ser Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
            180                 185                 190

Phe Thr Leu Thr Ile Ser Arg Leu Glu Pro Glu Asp Phe Ala Val Tyr
        195                 200                 205

Tyr Cys Gln Gln Thr Gly Arg Ile Pro Pro Thr Phe Gly Gln Gly Thr
    210                 215                 220

Lys Val Glu Ile Lys Ser Ser Ser Gly Ser Ser Ser Gly Ser
225                 230                 235                 240

Ser Ser Ser Gly Ala Pro Thr Arg Ser Pro Ile Thr Val Thr Arg Pro
                245                 250                 255

Trp Lys His Val Glu Ala Ile Lys Glu Ala Leu Asn Leu Leu Asp Asp
            260                 265                 270

Met Pro Val Thr Leu Asn Glu Glu Val Glu Val Val Ser Asn Glu Phe
        275                 280                 285

Ser Phe Lys Lys Leu Thr Cys Val Gln Thr Arg Leu Lys Ile Phe Glu
```

-continued

```
            290                 295                 300
Gln Gly Leu Arg Gly Asn Phe Thr Lys Leu Lys Gly Ala Leu Asn Met
305                 310                 315                 320

Thr Ala Ser Tyr Tyr Gln Thr Tyr Cys Pro Pro Thr Pro Glu Thr Asp
                325                 330                 335

Cys Glu Thr Gln Val Thr Thr Tyr Ala Asp Phe Ile Asp Ser Leu Lys
                340                 345                 350

Thr Phe Leu Thr Asp Ile Pro Phe Glu Cys Lys Lys Pro Val Gln Lys
            355                 360                 365
```

ANTI-EDB ANTIBODY-TARGETED IL-10 CYTOKINE FOR THERAPY OF RHEUMATOID ARTHRITIS

This is a National Phase Application filed under 35 U.S.C. §371 as a national stage of PCT/EP2007/004044, filed on May 8, 2007, an application claiming the benefit under 35 U.S.C. §119 of European Patent Application No. 06009456.2, filed on May 8, 2006, the content of each of which is hereby incorporated by reference in its entirety.

FIELD OF THE INVENTION

The present invention relates to fusion proteins comprising an antibody, functional fragment or functional derivative thereof having specific binding affinity to either the extracellular domain of oncofetal fibronectin (ED-B) or to at least one of the extracellular domains of oncofetal tenascin fused to a cytokine selected from the group consisting of IL-10, IL15, IL-24 and GM-CSF, functional fragments and functional derivatives thereof. The invention is also directed to the use of at least one of said fusion proteins for the manufacture of a medicament. In particular, the invention concerns the use of said medicament for the treatment of tumors or chronic inflammatory diseases such as atherosclerosis, arthritis and psoriasis.

The Sequence Listing submitted in text format (.txt) on Jun. 29, 2011, named "29726U_062011_ST25.txt", (created on Jun. 28, 2011, 42.9 KB), is incorporated herein by reference.

RELEVANT BACKGROUND OF THE INVENTION

Cytokines are immunomodulatory proteins, some of which have been used preclinically and clinically not only to fight cancer, but also to interfere with chronic inflammatory conditions and with infectious disease.

The therapeutic potential of recombinant cytokines is often limited by severe side effects even at low concentrations, thus preventing sufficient cytokine concentrations at the target tissues. Recently, monoclonal antibodies have been employed to target and deliver cytokines to sites of disease for increasing their potency and sparing normal tissue from toxic effects. Indeed, a number of antibody-cytokine fusion proteins have already been investigated for application in cancer therapy, often with impressive results. For example, the human antibody L19 specific to the ED-B domain of fibronectin (a marker of angiogenesis) has been used to deliver pro-inflammatory cytokines (such as IL-2, IL-12 or TNF) to solid tumors, sometimes with striking therapeutic benefits [for a review and corresponding references see Neri & Bicknell, Nat. Rev. Cancer (2005) 5:436-446, and also WO 01/62298]. However, many cytokines have a history of clinical failure, both, when used as a single agent or as fusion partners with monoclonal antibodies. For example, recombinant IL-2 ("Proleukin", Chiron) has been approved for the treatment of patients with renal cell carcinoma but response rates are typically low (generally below 20%) for this indication and even lower for other types of cancer. Other cytokines (such as interleukin-12 or interleukin-10, see below) have failed to demonstrate substantial efficacy in a series of clinical studies which has slowed clinical development programs. These cytokines are not yet approved as biopharmaceuticals. Interferon gamma is another example of a cytokine approved for a very narrow indication (treatment of chronic granulomatous disease, Genentech) which has failed to demonstrate substantial clinical benefits for other indications.

Even when fused to antibodies a striking gain in therapeutic index is unpredictable. For example, the anti-GD2 antibody-IL2 fusion EMD273063 failed to demonstrate substantial therapeutic benefits in a number of clinical trials, last but not least a trial in children with neuroblastoma (Osenga et al., Clin. Cancer Res. March 15; 12(6):1750-9 (2006)).

Interleukin-10 (IL-10) is a homodimeric cytokine produced by activated monocytes and T cells that is deeply involved in the regulation of inflammatory responses and immune reactions. Its main overall function is best described as dampener of immune responses, but IL-10 also possesses stimulatory activities. IL-10 was first described as cytokine synthesis inhibitory factor (CSIF), an activity produced by mouse Th2 cells that inhibited activation of and cytokine production by Th1 cells [Fiorentino et al., J. Exp. Med. 170 (6): 2081-95 (1989)]. The gene encoding human IL-10 is located on chromosome 1 [Kim et al., J. Immunol. 148(11): 3618-23 (1992)] and is translated into a protein composed of 160 amino acids with a molecular mass of 18.5 kDa. Human IL-10 is active as a non-disulfide-linked homodimer of 37 kDa [Syto et al., Biochemistry 37(48): 16943-51 (1998)].

IL-10 has been considered an attractive candidate for therapeutic use based on its potent in vitro immunomodulating activities and proven effects in animal models of acute and chronic inflammation, autoimmunity, cancer and infectious disease. Schering-Plough developed recombinant human IL-10 (ilodecakin, Tenovil®) for clinical trials. The protein is produced in E. coli and consists of 161 amino acids, identical with the endogenous human protein except for a methionine residue at the amino-terminus. Phase I and II clinical trials investigating safety, tolerance, pharmacokinetics, pharmacodynamics, immunological and hematological effects of single or multiple doses of IL-10 administered by intravenous or subcutaneous routes have been performed in various settings on healthy volunteers and specific patient populations [Moore et al., Annu Rev. Immunol. 19: 683-765 (2001)]. Clinical development though has been discontinued due to lack of efficacy of the compound. Recently, data has been presented which may explain, at least in part, the dilemma of IL-10 therapy. Tilg et al. found that high doses of IL-10 upregulate the production of IFN-gamma and neopterin, thereby counterbalancing its immunosuppressive properties. The authors concluded that the therapeutic action of systemically administered huIL-10 is limited by proinflammatory effects of the cytokine and suggest that this problem may be circumvented by approaches that result in effective mucosal delivery without causing an increase in systemic IL-10 concentrations [Tilg et al., Gut 50(2): 191-5 (2002)].

Interleukin-15 (IL-15) is a 14 to 15 kDa member of the 4α-helix bundle family of cytokines composed of 114 amino acids. In particular, IL-15 protein is posttranscriptionally regulated by multiple controlling elements that inhibit translation, including 12 upstream AUGs of the 5' untranslated region (UTR), 2 unusual signal peptides (the short peptide with 21 amino acids stays intracellularly, the long peptide with 48 amino acids is for secretion) and the C-terminus of the mature protein [Bamford et al., J. Immunol., 160(9): 4418-26 (1998)]. There is 97% sequence identity between human and simian IL-15 and 73% between human and mouse. This appears to be sufficient for huIL-15 to render it biologically active on simian and murine cells. IL-15 uses two distinct receptors and signalling pathways: A high affinity IL-15R system consisting of IL-2/15β, $\gamma_c$ and IL-15Rα subunits is expressed on T and NK cells. The IL-2/15R β and the $\gamma_c$ subunits are shared with IL-2 receptor [Giri et al., EMBO J., 3(12):2822-30 (1994)]. Mast cells respond to IL-15 with a receptor system that does not share elements with the IL-2 receptor but uses a novel 60 to 65 kDa IL-15RX subunit. A variety of tissues such as placenta, skeletal muscles, kidney, fibroblasts, epithelial cells, dendritic cells and monocytes express IL-15.

IL-15 stimulates the production of proinflammatory cytokines (e.g. TNFα, IL-1, IFNγ), the proliferation and Ig synthesis of activated B cells, the activation of $T_H1$, monocytes and lymphokine activated killer cells, the proliferation of mast cells and T cells and inhibits the apoptosis of T and B cells. In addition to the mentioned functional activities IL-15 plays a pivotal role in the development, survival and function of NK cells [Joost J. Oppenheim et al., Cytokine Reference; 213-221, (2002)]. In vivo studies demonstrated that exogenous IL-15 enhances the antitumor activity of tumor reactive $CD8^+$ T cells [Fehniger et al., Cytokine Growth Factor Rev., 13(2): 169-83 (2002)].

Abnormal high levels of IL-15 expression have been reported in inflammatory, neoplastic diseases and autoimmune diseases, e.g. rheumatoid arthritis, ulcerative colitis, Crohn's disease and multiple sclerosis [Joost J. Oppenheim et al., Cytokine Reference; 213-221, (2002)].

Because IL-2 and IL-15 use the same receptor subunits they share many features. The major differences are their sites of synthesis and secretion. IL-2 is produced by activated T-cells. In contrast, IL-15 is expressed in a variety of tissues as mentioned above. While IL-2 can promote apoptosis and limited $CD8^+$ memory T-cell survival and proliferation, IL-15 helps maintain memory $CD8^+$ population and can inhibit apoptosis. IL-15, initially thought to mediate similar biological effects as IL-2, has been shown to have unique properties in basic and pre-clinical studies that may be of benefit in the immunotherapy of cancer [Fehniger et al., Cytokine Growth Factor Rev., (2):169-83 (2002)]. Also, the toxicity profile of IL-15 resembles that of IL-2 very closely [Munger et al., Cell Immunol., 5(2):289-93 (1995)], thus suggesting targeted delivery of IL-15 to be superior to systemic delivery in terms of therapeutic index.

Studies to identify the epitopes of IL-15 that are responsible for binding to the IL-15 receptor revealed IL-15 mutants that showed either agonist or antagonist properties which may be useful as therapeutic agents [Bernard et al., J. Biol. Chem., 279(23): 24313-22 (2004)]. The IL-15 mutants IL-15D8S and IL-15Q108S were inactive in a CTLL-2 bioassay, but were able to competitively inhibit the biological activity of unmodified IL-15 [Pettit et al., J. Biol. Chem., 272(4): 2312-8 (1997)].

The melanoma differentiation associated gene-7 (mda-7=IL-24) was first identified in the 1990's as a consequence of its property of being induced during melanoma differentiation. It is a member of the IL-10 family of cytokines. The IL-24 gene cDNA encodes a 206 amino acid protein with 23.8 kDa. In human cells the secreted protein has a significantly higher molecular weight (40 kDa) due to heavy N-glycosylation compared to the intracellular protein (30/23 kDa). The homology of human IL-24 to the rat counterpart (MOB-5) is 68% and to the mouse one (FISP) 69%. There are two functional heterodimeric receptors for IL-24: IL-20R1/IL-20R2 and IL-22R1/IL-20R2 [Wang et al., Genes Immun., 5(5):363-70 (2004)], [Chada et al., Mol. Ther., 10(6):1085-95 (2004)]. Although IL-20R1 and IL-22R1 receptor chains are widely expressed the restricted expression of the common IL-20R2 in certain non-hemopoietic tissues suggests a pleiotropic role of IL-24 outside the hemopoietic system [Wolk et al., J. Immunol., 168(11): 5397-402 (2002)]. IL-24 is expressed by monocytes, T cells, dendritic cells and melanocytes. IL-24 induces the secretion of IFNγ, IL-6, TNFα, IL-1-β and GM-CSF indicating its function as a pro-Th1 cytokine. IL-10 (Th2 cytokine) inhibits the IL-24 activity.

The amount of IL-24 deposit is inversely correlated with melanoma progression. These findings lead to the hypothesis that mda-7 production is lost during melanoma invasion suggesting a role of IL-24 as a tumor suppressor [Chada et al., Mol. Ther., 10(6):1085-95 (2004)].

Expression of IL-24 in tumors may promote antigen presentation by activation or stimulation of immune accessory and effector cells [Chada et al., Mol. Ther., 10(6):1085-95 (2004)].

A large body of data demonstrates that overexpression of the IL-24 gene using either plasmid vectors or a replication defective adenovirus results in growth suppression and induction of apoptosis through activation of intracellular signalling pathways in a broad range of cancer cells. This kind of gene transfer exhibits minimal toxicity on normal cells while inducing potent apoptosis in a variety of cancer cells [Sieger et al., Mol. Ther., 9(3):355-67 (2004)]. A phase I dose escalation clinical trial, where adenoviral constructs expressing the IL-24 were administrated to 22 patients with advanced cancer, resulted in IL-24 expression, induction of apoptosis in all tumors and patients showed increases in $CD3^+CD8^+$ T cells after treatment. [Tong et al., Mol. Ther., 11(1):160-72 (2005)]. Different gene transfer studies of IL-24 noted that the tumors were smaller and appeared less vascularized compared to control tumors, which indicates antiangiogenic activity of IL-24 [Saeki et al., Oncogene., 21(29): 4558-66 (2002)]. When using adenovirus mda-7 (Ad-mda7) it is to be noted that there are potential drawbacks for its application in a clinical setting: first of all, ex vivo transduction of human cancer cells obtained from cancer patients with Ad-Mda7 followed by reintroduction into cancer patients is not practical; secondly, intratumoral administration of Ad-mda7 to generate a potent antitumor immune response is applicable only to localized tumors and not for disseminated tumors. Thus, alternative approaches need to be developed [Miyahara et al., Cancer Gene Ther. 2006].

Granulocyte-macrophage colony-stimulating factor (GM-CSF) is a 141 amino acid (mouse)/144 amino acid (human) protein containing a 17 amino acid secretion sequence. The apparent molecular weight of the mature glycosylated protein is 14-33 kDa, which is very resistant to denaturing and proteolytic conditions. The in vivo activities of GM-CSF are mediated by binding to high-affinity receptors comprising a GM-CSF-specific α chain and, for humans, a signal transducing β subunit that is shared with the IL-3 and the IL-5 receptors [Joost J. Oppenheim et al., Cytokine Reference, 899-908, 2002].

GM-CSF is a major regulator of granulocyte and macrophage lineage. It stimulates the survival, proliferation and differentiation of hematopoietic colony-forming cells of the neutrophil, macrophage and eosinophil lineages. In addition, it maintains the survival of hematopoietic colony-forming cells of the megakaryocytic and erythroid cell lineages [Joost J. Oppenheim et al., Cytokine Reference, 899-908, 2002]. It is also a potent immunostimulator with pleiotropic effects, including the augmentation of Ag presentation in a variety of cells, increased expression of MHC class II on monocytes and amplification of T cell proliferation [Fischer et al., J. Immunol., 141(11):3882-8 (1988), Smith et al., J. Immunol., 144 (10):3829-34 (1990), Morrissey et al., J. Immunol., 139(4): 1113-9 (1987)].

In pathology overexpression of GM-CSF may lead to inflammatory reactions (e.g. rheumatoid arthritis), toxic shock, blindness and autoimmunity while subphysiological levels may be involved in some cases of alveolar proteinosis. Alveolar proteinosis is a fatal lung disease where surfactant proteins accumulate in the lung due to a defect in macrophage-mediated clearance [Joost J. Oppenheim et al., Cytokine Reference; 899-908, 2002].

In animal models vaccination of mice bearing B16 melanoma with additional irradiated tumor cells expressing murine granulocyte-macrophage colony-stimulating factor (GM-CSF) stimulated a potent, long-lasting and specific anti-tumor immunity by increasing the immunogenicity of the tumors [Dranoff et al., Proc. Natl. Acad. Sci. USA., 90(8): 3539-43 (1993)]. Additionally, GM-CSF is widely used in oncology to reduce chemotherapy-related neutropenia, a reduction of neutrophils caused by chemotherapeutic drugs [Danova et al., Haematologica., 82(5):622-9 (1997)], Nose et al., J. Clin. Oncol., 13(4):1023-35 (1995)]. There is a threshold above which a GM-CSF based vaccine not only loses its efficacy but more importantly results in substantial immunosuppression in vivo. The dual effects of GM-CSF are mediated by the systemic and not the local concentration of this cytokine [Serafini et al., Cancer Res., 64(17):6337-43 (2004)]. Serious adverse events are seen at doses of 16 µg/kg per day for humans [Joost J. Oppenheim et al., Cytokine Reference; 899-908 (2002)].

Fibronectins are high molecular weight adhesive glycoproteins present in soluble form in plasma and other body fluids and in insoluble form in the extracellular matrix. EDB is a 91-amino-acid type III homology domain that is inserted into the fibronectin molecule by a mechanism of alternative splicing at the level of the primary transcript whenever tissue remodelling takes place [Zardi et al., Embo J. 6(8): 2337-42 (1987)].

EDB is essentially undetectable in healthy adult tissues. Its expression is strongly associated with the remodelling of the extracellular matrix and angiogenesis. The domain is abundant in many aggressive tumors and depending on the tumor type displays either predominantly vascular or diffuse stromal patterns of expression [Carnemolla et al., J. Cell Biol. 108(3): 1139-48 (1989)]. Despite its very restricted expression in normal tissues and its strong expression in many solid tumors the function of EDB does not seem to be indispensable because mice lacking the EDB exon develop normally, are fertile and heal bone fractions. Furthermore, double knockout mice lacking the EDB exon and p53 did not show any difference in the duration of survival compared to animals expressing EDB [Fukuda et al., Cancer Res 62(19): 5603-10 (2002)].

Because the EDB sequence is identical in mouse, rat, rabbit, dog, monkey and man it has not yet been possible to raise antibodies against this domain by hybridoma technology due to natural tolerance. A few years ago high affinity scFv antibody fragments (L19) against EDB were isolated by phage display technology [Carnemolla et al., Int. J. Cancer 68(3): 397-405 (1996); Neri et al., Nat. Biotechnol. 15(12): 1271-5. (1997); Pini et al., J. Biol. Chem. 273(34): 21769-76 (1998)]. L19 is able to stain tumor blood vessels in a wide range of experimental tumor models and on sections of human tumors and other angiogenic disorders [Carnemolla et al., J. Cell Biol. 108(3): 1139-48 (1989); Kaczmarek et al., Int. J. Cancer 59(1): 11-6 (1994); Berndt et al., Histochem. Cell Biol. 109 (3): 249-55 (1998)]. Castellani et al. have shown that L19 stains tumor blood vessels in grade III-IV astrocytomas but less than 10% of the vessels in grade I-II astrocytomas, suggesting that the expression of EDB in these lesions could be used for grading of the tumors [Castellani et al., Am. J. Pathol. 161(5): 1695-700 (2002)].

Due to the conservation of the antigen the targeting performance of L19 could be investigated in immunocompetent syngeneic animal models. Biodistribution studies with different radiolabelled antibody formats (scFv, small immuno protein/SIP and IgG) showed a preferential accumulation of up to 20% injected dose per gram of tissue (% ID/g) of L19 at the tumor site [Borsi et al., Blood 102(13): 4384-92 (2003)]. First immunoscintigraphy studies in human cancer patients with L19-diabody labelled with $^{123}$I confirmed that the antibody also localizes to human solid tumors and metastases [Santimaria et al., Clin. Cancer Res. 9(2): 571-9 (2003)].

The EDB domain of fibronectin is a good-quality marker of angiogenesis, which is overexpressed in a variety of solid tumors (e.g., renal cell carcinoma, colorectal carcinoma, hepatocellular carcinoma, high-grade astrocytomas, head and neck tumors, bladder cancer, etc.) but is virtually undetectable in normal adult tissues (exception made for the endometrium in the proliferative phase and some vessels in the ovaries). However, EDB is only weakly expressed in most forms of breast cancer, prostate cancer and some types of lung cancer, thus stimulating the search for novel vascular tumor antigens, which could be used for the antibody-mediated targeted delivery of therapeutic cytokines to these neoplasias.

In addition to EDB the extracellular domains of oncofetal tenascin have been established as an interesting target in therapy. Splice isoforms of tenascin-C are considered targets for antibody-based therapeutic strategies, particularly for those tumor classes in which low levels of EDB can be detected. Tenascin-C is a glycoprotein of the extracellular matrix. It comprises several fibronectin type 3 homology repeats that can be either included or omitted in the primary transcript by alternative splicing, leading to small and to large isoforms that have distinct biological functions. While the small isoform is expressed in several tissues the large isoform of tenascin-C exhibits a more restricted expression pattern. It is virtually undetectable in healthy adult tissues but is expressed during embryogenesis and is again expressed in adult tissues undergoing tissue remodelling including neoplasia. Its expression is localized around vascular structures in the tumor stroma of a variety of different tumors including breast carcinoma, oral squamous cell carcinoma, lung cancer, prostatic adenocarcinoma, colorectal cancer or astrocytoma and other brains tumors. Traditionally, the scientific community referred to the large isoform of tenascin-C for tenascin molecules, which would putatively comprise all alternatively spliced domains, and to the small isoform of tenascin-C whenever these domains were absent. Carnemolla and colleagues reported that the alternatively spliced domain C of tenascin-C exhibited a more restricted pattern of expression when compared to other alternatively spliced domains. It remained unclear at that time whether other alternatively spliced domains of tenascin-C also exhibited restricted incorporation into the tenascin molecule, and whether it would be more appropriate to evaluate the individual spliced domains separately as targets for antibody-based therapeutic strategies. Radiolabelled antibodies specific for domains A1 and D of tenascin-C were successfully employed in the clinic for the treatment of glioma and lymphoma. Furthermore, efficient tumor targeting by anti-tenascin antibodies has been demonstrated clinically using an avidin/biotin-based pre-targeting approach or, more recently, with monoclonal antibodies specific for the small isoform of tenascin-C. However, all these antibodies are of murine origin and, therefore, are most probably not suitable for repetitive administration to human patients and the development of biopharmaceuticals. For these reasons human antibodies specific to domains A1, C and D of tenascin-C were generated using antibody phage technology [PCT/EP2005/011624 of Philogen S.p.A].

As demonstrated above, there is still a high uncertainty involved in the field regarding the therapeutic utility of cytokines in general, in particular the therapeutic utility of cytokines for treating tumours and/or inflammatory diseases. Although the prior art sporadically indicates that some specific antibody-cytokine fusion proteins might allow for target-directed therapeutic treatment, there is still no reasonable expectation of success because the results are not predictable. The skilled person is left guessing with respect to the nature of a therapeutically useful cytokine and the effect that its combination with an antibody or derivative thereof would have. Therefore, the skilled person requires inventive skill to select the right combination of the many known cytokines and the many known targeting antibodies because the outcome cannot be predicted.

It is the object of the present invention to provide novel therapeutic substances for the treatment of cancer and/or inflammatory diseases, in particular for treating psoriasis, atherosclerosis and arthritis, that allow for the targeted delivery of the therapeutic substance to the sites of disease, which in turn allows for concentrating the medicament and reducing the toxic load for the remaining healthy tissues.

DESCRIPTION OF THE INVENTION

It was surprisingly found that the specific combination of an antibody targeting either the extracellular domain of oncofetal fibronectin (ED-B) or the extracellular domains of oncofetal tenascin fused to a cytokine selected from the group consisting of (a) IL-10, (b) IL15, (c) IL-24 and (d) GM-CSF provides for a new and therapeutically effective fusion protein.

Therefore, the above object is solved by providing a fusion protein comprising:
  (i) an antibody, functional fragment or functional derivative thereof having a specific binding affinity to either the extracellular domain of oncofetal fibronectin (ED-B) or to at least one of the extracellular domains of oncofetal tenascin fused to
  (ii) a cytokine selected from the group consisting of (a) IL-10, (b) IL15, (c) IL-24 and (d) GM-CSF, functional fragments and functional derivatives thereof.

The term "specific binding affinity" as it is used herein is to be understood to mean that the antibody, functional fragment or functional derivative thereof specifically binds to the target protein with significant affinity and not to other proteins with significant affinity that are also located in the same environment, i.e. assay system or body, organ, etc., in vivo or in vitro, and under the same conditions, e.g. pH, temperature, buffer, etc. In general, a binding specificity is tested by performing a binding assay with a specific target molecule and with a large number of non-related substances. Furthermore, functional tests, immunohistochemistry and other procedures can be used to assess the binding specificity of a specified antibody.

For many bioassays (e.g. ELISA) based on antibodies, functional fragments or functional derivatives thereof capable of specific binding, a dissociation constant of 1 micromolar or lower is required to yield detectable binding signals which are often associated with a specific binding mode. Preferably, the antibodies, functional fragments or functional derivatives for use in the present invention have a specific binding affinity corresponding to a dissociation constant of less than about 5, preferably about 1 or less micromolar (µM), more preferably about 0.1 µM or less, most preferably about 1 nM or less or even 1 pM or less.

Antibodies, functional fragments and functional derivatives thereof for practicing the invention are routinely available by hybridoma technology (Kohler and Milstein, Nature 256, 495-497, 1975), antibody phage display (Winter et al., Annu. Rev. Immunol. 12, 433-455, 1994), ribosome display (Schaffitzel et al., J. Immunol. Methods, 231, 119-135, 1999) and iterative colony filter screening (Giovannoni et al., Nucleic Acids Res. 29, E27, 2001) once the target antigen is available. Typical proteases for fragmenting antibodies into functional products are well-known. Other fragmentation techniques can be used as well as long as the resulting fragment has a specific high affinity and, preferably a dissociation constant in the micromolar to picomolar range.

The vascular tumour targeting performance of antibody fragments in scFv format has been shown to crucially depend (at least for a micromolar to picomolar dissociation constant) on the affinity of the antibody to the target. For example, the high affinity antibody fragment scFv(L19), specific for the ED-B domain of fibronectin, a marker of angiogenesis, was shown to target tumour neo-vasculature more efficiently than the parental antibody fragment scFv(E1), with a lower affinity for the antigen [Viti et al., Cancer Res. 15; 59(2):347-52 (1999)]. In certain cases binding avidity (e.g., associated with certain homobivalent antibody formats) can compensate for a moderate monomeric binding affinity [Nielsen et al., Cancer Res., 60(22):6434-40 (2000)].

A very convenient antibody fragment for targeting applications is the single-chain Fv fragment, in which a variable heavy and a variable light domain are joined together by a polypeptide linker. Other antibody fragments for vascular targeting applications include Fab fragments, $Fab_2$ fragments, miniantibodies (also called small immune proteins), tandem scFv-scFv fusions as well as scFv fusions with suitable domains (e.g. with the Fc portion of an immunoglobulin). For a review on certain antibody formats, see Holliger P, Hudson P J.; Engineered antibody fragments and the rise of single domains. Nat. Biotechnol. 2005 September, 23(9):1126-36).

The term "functional derivative" of an antibody for use in the present invention is meant to include any antibody or fragment thereof that has been chemically or genetically modified in its amino acid sequence, e.g. by addition, substitution and/or deletion of amino acid residue(s) and/or has been chemically modified in at least one of its atoms and/or functional chemical groups, e.g. by additions, deletions, rearrangement, oxidation, reduction, etc. as long as the derivative has substantially the same binding affinity as to its original antigen and, preferably, has a dissociation constant in the micro-, nano- or picomolar range. A most preferred derivative of the antibodies for use in the present invention is an antibody fusion protein that will be defined in more detail below.

In a preferred embodiment, the antibody, fragment or functional derivative thereof for use in the invention is one that is selected from the group consisting of polyclonal antibodies, monoclonal antibodies, chimeric antibodies, humanized antibodies, CDR-grafted antibodies, Fv-fragments, Fab-fragments and $Fab_2$-fragments and antibody-like binding proteins, e.g. affilines, anticalines and aptamers.

For a review of antibody-like binding proteins see Binz et al. on engineering binding proteins from non-immunoglobulin domains in Nature Biotechnology, Vol. 23, No. 10, October 2005, 12571268. The term "aptamer" describes nucleic acids that bind to a polypeptide with high affinity. Aptamers can be isolated from a large pool of different single-stranded RNA molecules by selection methods such as SELEX (see, e.g., Jayasena, Clin. Chem., 45, p. 1628-1650, (1999); Klug and Famulok, M. Mol. Biol. Rep., 20, p. 97-107 (1994); U.S.

Pat. No. 5,582,981). Aptamers can also be synthesized and selected in their mirror form, for example, as the L-ribonucleotide (Nolte et al., Nat. Biotechnol., 14, pp. 1116-1119, (1996); Klussmann et al., Nat. Biotechnol., 14, p. 1112-1115, (1996)). Forms isolated in this way have the advantage that they are not degraded by naturally occurring ribonucleases and, therefore, have a greater stability.

Another antibody-like binding protein and alternative to classical antibodies are the so-called "protein scaffolds", for example, anticalines, that are based on lipocaline (Beste et al., Proc. Natl. Acad. Sci. USA, 96, p. 1898-1903, (1999)). The natural ligand binding sites of lipocalines, for example, of the retinol-binding protein or bilin-binding protein, can be changed, for example, by employing a "combinatorial protein design" approach, and in such a way that they bind selected haptens (Skerra, Biochem. Biophys. Acta, 1482, pp. 337-350, (2000)). For other protein scaffolds it is also known that they are alternatives for antibodies (Skerra, J. Mol. Recognit, 13, pp. 167-287, (2000)). (Hey, Trends in Biotechnology, 23, pp. 514-522, (2005)).

According to the invention the term functional antibody derivative is meant to include said protein-derived alternatives for antibodies, i.e. antibody-like binding proteins, e.g. affilines, anticalines and aptamers that specifically recognize at least one extracellular domain of oncofetal fibronectin or oncofetal tenascin.

In summary, the terms antibody, functional fragment and functional derivative thereof denote all substances that have the same or similar specific binding affinity to any one of the extracellular domains of oncofetal fibronectin or oncofetal tenascin as a complete antibody having specific binding affinity to these targets.

For tenascin there are a number of isoforms available, e.g. tenascin-C, tenascin-R and tenascin-X. For practicing the present invention the extracellular domains of the large isoform of tenascin-C are most preferred as specific targets for the antibody, functional fragment or functional derivative thereof that is part of the fusion proteins of the present invention.

In a preferred embodiment the antibody, functional fragment or functional derivative thereof, that is part of a fusion protein of the invention, has a specific binding affinity to at least one of the extracellular domains of oncofetal tenascin-C, more preferably to at least one of the extracellular domains of the large isoform of tenascin-C.

The extracellular domains of tenascin-C are denoted domains A1, A2, A3, A4, B, C and D. There are already a number of antibodies available that are directed against one of these domains (see Siri A. et al., Different susceptibility of small and large human tenascin-C isoforms to degradation by matrix metalloproteinases. J. Biol. Chem., Apr. 14, 1995, 270(15):8650-4; Carnemolla B. et al., Identification of a glioblastoma-associated tenascin-C isoform by a high affinity recombinant antibody. Am. J. Pathol. May 1999, 154(5):1345-52; Silacci M. et al., Human monoclonal antibodies to domain C of tenascin-C selectively target solid tumors in vivo. Protein Eng. Des. Sel. October 2006, 19(10): 471-8).

In a more preferred embodiment the present invention relates to fusion proteins of the invention comprising an antibody, functional fragment or functional derivative thereof having specific binding affinity to any one of the extracellular domains of tenascin-C, i.e. A1, A2, A3, A4, B, C and D, preferably to any one of the domains A1, C or D, more preferably to the domain C of tenascin-C.

The term "fusion protein" as it is used in the context of the present invention is meant to encompass all conjugates, wherein said antibody, fragment or functional derivative is somehow bound to a cytokine selected from the group consisting of (a) IL-10, (b) IL15, (c) IL-24 and (d) GM-CSF, functional fragments and functional derivatives thereof, by, e.g. covalent and/or non-covalent, e.g. ionic bonds. The term encompasses both binding arrangements, i.e. antibody-cytokine or cytokine-antibody.

The terms functional fragment and functional derivative with regard to said cytokines are to be interpreted essentially in analogy to the same terms for antibodies. Functional fragments and derivatives of cytokines are those that essentially have the same physiological function/activity as the naturally occurring cytokines. For example, preferred assays for determining the function/activity of the cytokines, fragments and derivatives thereof for preparing fusion proteins according to the present invention are:

The cytokine activity/function of IL-10 or functional derivatives thereof can be determined by performing a proliferation assay on murine mast cells MC/9. For example, said cells are cultured in DMEM medium containing 10% FBS, 10% Rat T-Stim (Becton Dickinson), 1% antibiotic, 2 mM glutamine and 0.05 mM β-mercaptoethanol [Thompson-Snipes et al., J. Exp. Med. 173(2): 507-10 (1991)]. For preparing the assay 100 µl medium without Rat T-Stim are placed in each well of a 96-well flat-bottom tissue culture plate with ultra low attachment (Costar® 3474) except for the first row. 200 µl recombinant human (rhu) IL-10 (100 ng/ml) or an equivalent molar amount of the sample to be tested are placed in the wells of the first row. 1:2 serial dilutions across the rows of the microtiter plate are prepared by transferring 100 µl of the sample to the next well in the row and mixing starting form the first row. One row of wells contains only 100 µl assay medium (no cytokine) as a negative control. MC/9 cells are then counted and diluted to a concentration of $5 \times 10^5$ cells/ml. To remove residual cytokine the cells are washed twice with culture medium without Rat T-Stim by centrifuging the cells, aspirating the medium and resuspending them again in fresh medium. 100 µl of this cell suspension are added to the wells of the 96 well plate ($5 \times 10^4$ cells/well). After 48-72 hours 20 µl of 5 mg/ml MTT solution (in PBS, filtered), a substrate for the mitochondrial dehydrogenase, are added to the cells. 4 hours later, the plate is centrifuged at 2400 g for 10 minutes. The medium is aspirated and cells are lysed by adding 100 µl DMSO (Fluka 41641). Finally, the plates are read at 570 nm. Each concentration is performed in triplicates.

For example, the cytokine activity/function of huIL15 or functional derivatives thereof can be determined (Biosource Cytokine Facts handbook) by performing an assay on cytotoxic T lymphocytes line 2 (CTLL-2). Said cells are grown in RPMI medium containing 10% FBS, 1% antibiotics, 2 mM glutamine (100×), 1 mM Sodium pyruvate (100×) and 50 µM 2-mercaptoethanol (1000×). Additionally, the CTLL-2 cells require 20 U/ml huIL-2 (Roche 1 011 456). About one week before assay start the cells should be starved and receive only 10 U/ml huIL-2. Preparing the assay 50 µl CTLL-2 assay medium are added to each well of a 96-well flat-bottom tissue culture plate with ultra low attachment (Costar® 3474) expect of the first row. 100 µl recombinant human IL-15 standard (10 ng/ml) or an equimolar amount of a test sample are placed into the first well. 1:2 Serial dilutions are done by transferring 50 µl to the next well in the row starting at the first well. One row of wells contains only 50 µl assay medium (no rhuIL-15) as a negative control. CTLL-2 cells are counted and diluted to a concentration of $5 \times 10^5$ cells/ml. To remove residual huIL-2 the cells are washed as follows: After centrifuging the cells 5 minutes at 1100 rpm the medium is aspirated and the cell pellet is again suspended in fresh medium.

This washing procedure is repeated twice. 50 µl of cell suspension are added to each microtiter-plate well (5×10⁴ cells/well) and the plate is incubated at 37° C. and 5% $CO_2$. Measurements are done in triplicates. After 72 hours 20 µl of 5 mg/ml MTT (Sigma 206-069-5) solution (in PBS) is added to each well. 2 to 4 hours later the plate is centrifuged at 2400 g for 10 minutes. The medium is aspired and the cells are lysed by adding 100 µl DMSO (Fluke 41641). Then, the plate is read at 570 nm.

For example, in order to test the biological function/activity of IL-24 or a functional derivative thereof as a cytokine, its induction of secondary cytokine secretion (IL-6, TNFalpha and IFNgamma) by PBMC can be examined [Caudell et al., J. Immunol., 168(12):6041-6 (2002)]. Detection of the secondary cytokines can be done by specific ELISA(s).

Another option is to test the ability of IL-24 or a functional derivative thereof to selectively induce apoptosis in cancer cells [Sauane et al., Cancer Biol. Ther., 3(8):739-51 (2004)]. For doing this, cancer cells like DU-145, PC-3, LNCaP, MDA-MB-231 and others can be used. The cells are plated in 96-well dishes and allowed to attach for 12 h prior to IL-24 treatment (different concentrations, usually about 25-50 µg/ml). Cells are incubated for 5-7 days. Cell growth and viable cell numbers are monitored by MTT staining. The resulting absorbance measured at 570 nm is directly proportional to the number of viable cells.

For example, the cytokine activity/function of GM-CSF or a functional derivative thereof can be determined (Biosource Cytokine Facts handbook) by performing a proliferation assay on murine mast cells MC/9. Said cells are cultured in DMEM medium containing 10% FBS, 10% Rat T-Stim (Becton Dickinson), 1% antibiotic, 2 mM glutamine and 0.05 mM β-mercaptoethanol. RPMI medium containing 10% FBS, 1% antibiotics, 2 mM glutamine and 0.05 M β-mercaptoethanol is used as assay medium. For preparing the assay 100 µl assay medium are placed in each well of a 96-well flat-bottom tissue culture plate with ultra low attachment (Costar® 3474) except the first row. 200 µl recombinant muGM-CSF (5 ng/ml) or an equivalent molar amount of the sample are placed into the wells of the first row. 1:2 serial dilutions across the rows of the microtiter plate are done by transferring 100 µl of the sample to the next well in the row and mixing starting form the first row. One row of wells contains only 100 µl assay medium (no GM-CSF) as a negative control. MC/9 cells are counted and diluted to a concentration of 5×10⁴ cells/ml. To remove residual cytokine the cells are washed twice with RPMI by centrifuging the cells, aspirating the medium and resuspending them again in fresh RPMI. 100 µl of this cell suspension are added to the wells of a 96 well plate (5×10³ cells/well) which already contains 100 µl of the corresponding medium enriched with rmuGM-CSF or GM-CSF fusion protein. After 48-72 hours 20 µl of 5 mg/ml MTT solution (in PBS, filtered), a substrate for the mitochondrial dehydrogenase, are added to the cells. 4 hours later the plate is centrifuged at 2400 g for 10 minutes. The medium is aspirated and the cells are lysed by adding 100 µl DMSO (Fluka 41641). Finally, the plates are read at 570 nm. Each concentration is tested in triplicates.

In a preferred embodiment of the invention the fusion protein according to the invention comprises the diabody scFv L19 (long) having the amino acid sequence set forth in SEQ ID NO: 6.

In another preferred embodiment of the invention the fusion protein according to the invention comprises the diabody L19 (short) having the amino sequence set forth in SEQ ID NO: 7.

In a further preferred embodiment of the invention the fusion protein is one, wherein the antibody, functional fragment or functional derivative thereof having specific binding affinity to at least one of the extracellular domains of oncofetal tenascin is selected from the group consisting of F16 (long), F16 (short), F16 (A34M) (long), F16 (A34M) (short), G11 (long) and G11 (short) having the amino sequences set forth in SEQ ID NO: 8 to 13, respectively.

More preferably, the fusion protein according to the invention is one, wherein a member of the group consisting of L19 (long), L19 (short), F16 (long), F16 (short), F16 (A34M) (long), F16 (A34M) (short), G11 (long) and G11 (short) is fused to a cytokine selected from the group consisting of GM-CSF, IL-10, IL15 and IL-24, functional fragments and functional derivatives thereof.

For all embodiments and aspects of the present invention it is preferred that the cytokine is a murine or human, preferably a human cytokine, functional fragment or functional derivative thereof.

The fusion proteins according to the invention may be arranged such that the cytokine, functional fragment or functional derivative thereof is fused N-terminally or C-terminally to the antibody, functional fragment or functional derivative thereof.

It was surprisingly found that the short linker functional derivatives of L19, F16 and G11 result in an increased formation of diabodies when compared to the long linker variants. Furthermore, it was surprisingly noted that fusion proteins comprising scFv F16 (long or short) with a mutation at position 34 in the amino acid sequence (A->M) [SEQ ID NOS: 10 & 11] demonstrated much higher expression rates compared to the regular scFv F16 sequence.

Because of the above advantages of short variants, those fusion proteins according to the invention are preferred, wherein the antibody fragment or functional derivative thereof is selected from the group consisting of L 19 (short), F16 (short), F16 (A34M) (short) and G11 (short).

Fusion proteins comprising the F16 (A34M) variant (long or short) are more preferred and those comprising the short F16 (A34M) variant are most preferred.

As a matter of fact, in an independent aspect the present invention relates to a fusion protein comprising:
(i) F16 (A34M) (short or long, preferably short) having specific binding affinity to at least one of the extracellular domains of oncofetal tenascin fused to any cytokine, functional fragments and functional derivatives thereof.

In a preferred embodiment the fusion proteins according to the invention are selected from the group consisting of L19-IL-10, IL15-L19, IL-24-L19, L19-GM-CSF, L19-IL15, IL24-L19.

In another preferred embodiment the fusion proteins according to the invention are selected from the group consisting of those having the amino acid sequence set forth in SEQ ID NO: 14-19.

In another aspect the present invention relates to the use of a fusion protein according to the invention for the manufacture of a medicament.

In a preferred embodiment the present invention relates to the use of the above fusion proteins for the treatment of cancer in a mammal, preferably in a human.

In another preferred embodiment the present invention relates to the use of the above fusion proteins for the treatment of inflammatory diseases, preferably chronic inflammatory diseases in a mammal, preferably in a human.

Preferably, the inflammatory disease is selected from the group consisting of psoriasis, atherosclerosis, arthritis, preferably rheumatoid arthritis.

A further aspect of the present invention relates to a pharmaceutical composition comprising at least one fusion protein of the invention and optionally a pharmaceutically acceptable excipient.

Pharmaceutical compositions of the present invention typically comprise a therapeutically effective amount of a fusion protein according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilizers, antioxidants, pH-regulating substances, controlled-release excipients. The pharmaceutical preparation of the invention may be adapted, for example, for parenteral use and may be administered to the patient in the form of solutions or the like.

Finally, another aspect of the present invention concerns a method of treatment, wherein an effective amount of a pharmaceutical composition is administered to a patient in need thereof, preferably a patient suffering from cancer and/or inflammatory diseases.

In effecting treatment of a subject suffering from diseases or conditions described above, a fusion protein of the present invention can be administered in any form or mode which makes the therapeutic compound bioavailable in an effective amount, including oral or parenteral routes. For example, compositions of the present invention can be administered subcutaneously, intramuscularly, intravenously and the like. One skilled in the art in the field of preparing formulations can readily select the proper form and mode of administration depending upon the particular characteristics of the product selected, the disease or condition to be treated, the stage of the disease or condition and other relevant circumstances (see. e.g. Remington's Pharmaceutical Sciences, Mack Publishing Co. (1990)). The compositions of the present invention can be administered alone or in the form of a pharmaceutical preparation in combination with pharmaceutically acceptable carriers or excipients, the proportion and nature of which are determined by the solubility and chemical properties of the product selected, the chosen route of administration and standard pharmaceutical practice. The products of the present invention, while effective themselves, may be formulated and administered in the form of their pharmaceutically acceptable salts, such as acid addition salts or base addition salts, for purposes of stability, convenience of crystallization, increased solubility and the like.

SEQUENCE LISTINGS

SEQ ID NO: 1 shows the amino acid sequence of human IL-10; accession no: P22301 (SwissProt); Vieira et al., Proc. Natl. Acad. Sci. U.S.A. 88(4), 1172-1176 (1991).

MHSSALLCCLVLLTGVRASPGQGTQSENSCTHFPGNLPNMLRDLRDAF

SRVKTFFQMKDQLDNLLLKESLLEDFKGYLGCQALSEMIQFYLEEVMP

QAENQDPDIKAHVNSLGENLKTLRLRLRRCHRFLPCENKSKAVEQVKN

AFNKLQEKGIYKAMSEFDIFINYIEAYMTMKIRN

SEQ ID NO: 2 shows the amino acid sequence of human IL-15; accession no: P40933 (SwissProt); Grabstein et al., Science 264 (5161), 965-968 (1994).

NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

SEQ ID NO: 3 shows the amino acid sequence of human IL-24; accession no: Q13007 (SwissProt); Jiang et al., Oncogene 11 (12), 2477-2486 (1995).

AQGQEFHFGPCQVKGVVPQKLWEAFWAVKDTMQAQDNITSARLLQQEV

LQNVSDAESCYLVHTLLEFYLKTVFKNYHNRTVEVRTLKSFSTLANNF

VLIVSQLQPSQENEMFSIRDSAHRRFLLFRRAFKQLDVEAALTKALGE

VDILLTWMQKFYKL

SEQ ID NO: 4 shows the amino acid sequence of human GM-CSF; accession no: P04141 (SwissProt); Lee et al., Proc. Natl. Acad. Sci. U.S.A. 82 (13), 4360-4364 (1985).

APARSPSPSTQPWEHVNAIQEARRLLNLSRDTAAEMNETVEVISEMFD

LQEPTCLQTRLELYKQGLRGSLTKLKGPLTMMASHYKQHCPPTPETSC

ATQIITFESFKENLKDFLLVIPFDCWEPVQE

SEQ ID NO: 5 shows the amino acid sequence of murine GM-CSF; accession no: P01587 (SwissProt); Miyatake et al., EMBO J. 4 (10), 2561-2568 (1985).

APTRSPITVTRPWKHVEAIKEALNLLDDMPVTLNEEVEVVSNEFSFKK

LTCVQTRLKIFEQGLRGNFTKLKGALNMTASYYQTYCPPTPETDCETQ

VTTYADFIDSLKTFLTDIPFECKKPVQK

SEQ ID NO: 6 shows the amino acid sequence of L19 (long); Viti et al., Cancer Res., 59(2): 347-52 (1999).

EVQLLESGGGLVQPGGSLRLSCAASGFTFSSFSMSWVRQAPGKGLEWV

SSISGSSGTTYYADSVKGRFTISRDNSKNTLYLQMNSLRAEDTAVYYC

AKPFPYFDYWGQGTLVTVSSGDGSSGGSGGASTGEIVLTQSPGTLSLS

PGERATLSCRASQSVSSSYLAWYQQKPGQAPRLLIYYASSRATGIPDR

FSGSGSGTDFTLTISRLEPEDFAVYYCQQTGRIPPTFGQGTKVEIK
(Bold letters indicate the 14 amino acid linker)

SEQ ID NO: 7 shows the amino acid sequence of L19 (short) (not yet published).

EVQLLESGGGLVQPGGSLRLSCAASGFTFSSFSMSWVRQAPGKGLEWV

SSISGSSGTTYYADSVKGRFTISRDNSKNTLYLQMNSLRAEDTAVYYC

AKPFPYFDYWGQGTLVTVSSGSSGGEIVLTQSPGTLSLSPGERATLSC

RASQSVSSSFLAWYQQKPGQAPRLLIYYASSRATGIPDRFSGSGSGTD

FTLTISRLEPEDFAVYYCQQTGRIPPTFGQGTKVEIK
(Bold letters indicate the 5 amino acid linker.)

SEQ ID NO: 8 shows the amino acid sequence of F16 (long).

EVQLLESGGGLVQPGGSLRLSCAASGFTFSRYGASWVRQAPGKGLEWV
SAISGSGGSTYYADSVKGRFTISRDNSKNTLYLQMNSLRAEDTAVYYC
AKAHNAFDYWGQGTLVTVSRGGGGSGGGGSGGGGSSELTQDPAVSVAL
GQTVRITCQGDSLRSYYASWYQQKPGQAPVLVIYGKNNRPSGIPDRFS
GSSSGNTASLTITGAQAEDEADYYCNSSVYTMPPVVFGGGTKLTVLG

SEQ ID NO: 9 shows the amino acid sequence of F16 (short).

EVQLLESGGGLVQPGGSLRLSCAASGFTFSRYGASWVRQAPGKGLEWV
SAISGSGGSTYYADSVKGRFTISRDNSKNTLYLQMNSLRAEDTAVYYC
AKAHNAFDYWGQGTLVTVSRGSSGGSSELTQDPAVSVALGQTVRITCQ
GDSLRSYYASWYQQKPGQAPVLVIYGKNNRPSGIPDRFSGSSSGNTAS
LTITGAQAEDEADYYCNSSVYTMPPVVFGGGTKLTVLG
(Bold letters indicate the 5 amino acid linker.)

SEQ ID NO: 10 shows the amino acid sequence of F16 (A34M) (long).

EVQLLESGGGLVQPGGSLRLSCAASGFTFSRYG<u>M</u>SWVRQAPGKGLEWV
SAISGSGGSTYYADSVKGRFTISRDNSKNTLYLQMNSLRAEDTAVYYC
AKAHNAFDYWGQGTLVTVSRGGGGSGGGGSGGGGSSELTQDPAVSVAL
GQTVRITCQGDSLRSYYASWYQQKPGQAPVLVIYGKNNRPSGIPDRFS
GSSSGNTASLTITGAQAEDEADYYCNSSVYTMPPVVFGGGTKLTVLG
(The underlined amino acid indicates the
substitution of A to M.)

SEQ ID NO: 11 shows the amino acid sequence of F16 (A34M) (short).

EVQLLESGGGLVQPGGSLRLSCAASGFTFSRYG<u>M</u>SWVRQAPGKGLEWV
SAISGSGGSTYYADSVKGRFTISRDNSKNTLYLQMNSLRAEDTAVYYC
AKAHNAFDYWGQGTLVTVSRGSSGGSSELTQDPAVSVALGQTVRITCQ
GDSLRSYYASWYQQKPGQAPVLVIYGKNNRPSGIPDRFSGSSSGNTAS
LTITGAQAEDEADYYCNSSVYTMPPVVFGGGTKLTVLG
(The underlined amino acid indicates the
substitution of A to M. Bold letters indicate the
5 amino acid linker.)

SEQ ID NO: 12 shows the amino acid sequence of G11 (long).

EVQLVESGGGLVQPGGSLRLSCAASGFTFSGSRMGWVRQAPGKGLEWV
SAINEEGGQTYYADSVKGRFTISRDNSKNTLYLQMNSLRAEDTAVYYC
AKHPPHRPFDYWGQGTLVTVSRGGGGSGGGGSGGGGSSELTQDPAVSV
ALGQTVRITCQGDSLRLYYASWYQQKPGQAPVLVIYGKNNRPSGIPDR
FSGSSSGNTASLTITGAQAEDEADYYCNSSHGPRRPVVFGGGTKLTVL
G

SEQ ID NO: 13 shows the amino acid sequence of G11 (short).

EVQLVESGGGLVQPGGSLRLSCAASGFTFSGSRMGWVRQAPGKGLEWV
SAINEEGGQTYYADSVKGRFTISRDNSKNTLYLQMNSLRAEDTAVYYC
AKHPPHRPFDYWGQGTLVTVSRGSSGGSSELTQDPAVSVALGQTVRIT
CQGDSLRLYYASWYQQKPGQAPVLVIYGKNNRPSGIPDRFSGSSSGNT
ASLTITGAQAEDEADYYCNSSHGPRRPVVFGGGTKLTVLG

SEQ ID NO: 14 shows the amino acid sequence of fusion protein L19 (long)-huIL-10:

EVQLLESGGGLVQPGGSLRLSCAASGFTFSSFSMSWVRQAPGKGLEWV
SSISGSSGTTYYADSVKGRFTISRDNSKNTLYLQMNSLRAEDTAVYYC
AKPFPYFDYWGQGTLVTVSSGDGSSGGSGGASTGEIVLTQSPGTLSLS
PGERATLSCRASQSVSSSYLAWYQQKPGQAPRLLIYYASSRATGIPDR
FSGSGSGTDFTLTISRLEPEDFAVYYCQQTGRIPPTFGQGTKVEIKSS
SSGSSSSGSSSSGSPGQGTQSENSCTHFPGNLPNMLRDLRDAFSRVKT
FFQMKDQLDNLLLKESLLEDFKGYLGCQALSEMIQFYLEEVMPQAENQ
DPDIKAHVNSLGENLKTLRLRLRRCHRFLPCENKSKAVEQVKNAFNKL
QEKGIYKAMSEFDIFINYIEAYMTMKIRN

SEQ ID NO: 15 shows the amino acid sequence of fusion protein L19 (short)-huIL15:

EVQLLESGGGLVQPGGSLRLSCAASGFTFSSFSMSWVRQAPGKGLEWV
SSISGSSGTTYYADSVKGRFTISRDNSKNTLYLQMNSLRAEDTAVYYC
AKPFPYFDYWGQGTLVTVSSGSSGGEIVLTQSPGTLSLSPGERATLSC
RASQSVSSSFLAWYQQKPGQAPRLLIYYASSRATGIPDRFSGSGSGTD
FTLTISRLEPEDFAVYYCQQTGRIPPTFGQGTKVEIKSSSSGSSSSGS
SSSGNWVNVISDLKKIEDLIQSMHIDATLYTESDVHPSCKVTAMKCFL
LELQVISLESGDASIHDTVENLIILANNSLSSNGNVTESGCKECEELE
EKNIKEFLQSFVHIVQMFINTS

SEQ ID NO: 16 shows the amino acid sequence of fusion protein huIL15-L19 (short):

NWVNVISDLKKIEDLIQSMHIDATLYTESDVHPSCKVTAMKCFLLELQ
VISLESGDASIHDTVENLIILANNSLSSNGNVTESGCKECEELEEKNI
KEFLQSFVHIVQMFINTSSSSSGSSSSGSSSSGEVQLLESGGGLVQPG
GSLRLSCAASGFTFSSFSMSWVRQAPGKGLEWVSSISGSSGTTYYADS
VKGRFTISRDNSKNTLYLQMNSLRAEDTAVYYCAKPFPYFDYWGQGTL
VTVSSGSSGGEIVLTQSPGTLSLSPGERATLSCRASQSVSSSFLAWYQ
QKPGQAPRLLIYYASSRATGIPDRFSGSGSGTDFTLTISRLEPEDFAV
YYCQQTGRIPPTFGQGTKVEIK

SEQ ID NO: 17 shows the amino acid sequence of fusion protein huIL24-L19 (short):

AQGQEFHFGPCQVKGVVPQKLWEAFWAVKDTMQAQDNITSARLLQQEV

LQNVSDAESCYLVHTLLEFYLKTVFKNYHNRTVEVRTLKSFSTLANNF

VLIVSQLQPSQENEMFSIRDSAHRRFLLFRRAFKQLDVEAALTKALGE

VDILLTWMQKFYKLSSSSGSSSSGSSSSGEVQLLESGGGLVQPGGSLR

LSCAASGFTFSSFSMSWVRQAPGKGLEWVSSISGSSGTTYYADSVKGR

FTISRDNSKNTLYLQMNSLRAEDTAVYYCAKPFPYFDYWGQGTLVTVS

SGSSGGEIVLTQSPGTLSLSPGERATLSCRASQSVSSSFLAWYQQKPG

QAPRLLIYYASSRATGIPDRFSGSGSGTDFTLTISRLEPEDFAVYYCQ

QTGRIPPTFGQGTKVEIK

SEQ ID NO: 18 shows the amino acid sequence of fusion protein L19 (short) huGM-CSF:

EVQLLESGGGLVQPGGSLRLSCAASGFTFSSFSMSWVRQAPGKGLEWV

SSISGSSGTTYYADSVKGRFTISRDNSKNTLYLQMNSLRAEDTAVYYC

AKPFPYFDYWGQGTLVTVSSGSSGGEIVLTQSPGTLSLSPGERATLSC

RASQSVSSSFLAWYQQKPGQAPRLLIYYASSRATGIPDRFSGSGSGTD

FTLTISRLEPEDFAVYYCQQTGRIPPTFGQGTKVEIKSSSSGSSSSGS

SSSGAPARSPSPSTQPWEHVNAIQEARRLLNLSRDTAAEMNETVEVIS

EMFDLQEPTCLQTRLELYKQGLRGSLTKLKGPLTMMASHYKQHCPPTP

ETSCATQIITFESFKENLKDFLLVIPFDCWEPVQE

SEQ ID NO: 19 shows the amino acid sequence of fusion protein L19 (short)-murine GM-CSF:

EVQLLESGGGLVQPGGSLRLSCAASGFTFSSFSMSWVRQAPGKGLEWV

SSISGSSGTTYYADSVKGRFTISRDNSKNTLYLQMNSLRAEDTAVYYC

AKPFPYFDYWGQGTLVTVSSGSSGGEIVLTQSPGTLSLSPGERATLSC

RASQSVSSSFLAWYQQKPGQAPRLLIYYASSRATGIPDRFSGSGSGTD

FTLTISRLEPEDFAVYYCQQTGRIPPTFGQGTKVEIKSSSSGSSSSGS

SSSGAPTRSPITVTRPWKHVEAIKEALNLLDDMPVTLNEEVEVVSNEF

SFKKLTCVQTRLKIFEQGLRGNFTKLKGALNMTASYYQTYCPPTPETD

CETQVTTYADFIDSLKTFLTDIPFECKKPVQK

FIGURES

FIG. 1 illustrates the accumulation of the fusion proteins in subcutaneous F9 tumors in 129Sv mice. The biodistribution data demonstrate that all four fusion proteins have a higher uptake in the tumor compared to normal organs. Data at 24 h after injection of the radiolabelled proteins are shown for: A) L19-IL10, B) IL15-L19, C) IL24-L19, D) L19-GMCSF and E) L19-IL15

FIG. 2 Antibody-mediated Near-Infrared-Imaging of arthritic mice. Animals were injected with SIP(L19)-Alexa750 (a), SIP(G11)-Alexa750 (b) or control SIP-Alexa750 (c). Pictures were taken 24 h after injection of the fluorescently labelled antibodies. Arrows indicate grade 2 swelling at front paws of the mice.

FIG. 3 Accumulation of radiolabelled SIP(L19) and SIP(G11) in arthritic paws. Panel A shows the arthritic extremities of a mouse injected with SIP(L19)-$^{125}$I. The left paw was classified as grade 2, the right paw as grade 1 arthritis. Panel B displays the same experiment with SIP(G11)-$^{125}$I. Here the left paw was classified as grade 1, the right paw as grade 2 arthritis. Panel C shows a mouse injected with control SIP-$^{125}$I, an antibody that does not bind to any structure in the mouse. Here the left paw was classified as grade 2, the right paw as grade 1 arthritis.

FIG. 4 illustrates the targeting of cytokines to arthritic lesions. Arthritic mice were injected intravenously (i.v.) in the lateral tail vein with saline (black circles), with L19-IL2 (black triangles, dashed line), with L19-TNFalpha (crosses, dashed line) or with L19-IL10 (open squares) diluted in a volume of 200 μl of saline. Injections were started at day 1 after arthritis onset and then repeated every second day for 3 injections per animal as indicated by arrows. The cumulative doses for the fusion proteins were: 20 μg equivalents of IL2, 6 μg equivalents of TNFalpha and 150 μg equivalents of IL10 per mouse, respectively. Arthritic score was evaluated daily and was expressed as means±SEM. The swelling of the paws was measured every second day and the mean of all 4 paws was assigned as paw thickness to each animal. Results displayed are means±SEM of each group. Each group consisted of 7 mice.

FIG. 5 demonstrates that the targeted delivery of IL10 to sites of inflammation is superior to systemic IL10 treatment. Arthritic mice were injected intravenously (i.v.) in the lateral tail vein with saline (black circles), with L19-IL10 (open squares) or with HyHel10-IL10 (crosses, dashed line) diluted in a volume of 200 μl of saline. Injections were started at day 1 of arthritis onset and then repeated every second day for 3 injections per animal as indicated by arrows. The cumulative doses for the fusion proteins were 150 μg equivalents of IL10 per mouse. Arthritic score was evaluated daily and was expressed as means±SEM. The swelling of the paws was measured every second day and the mean of all 4 paws was assigned as paw thickness to each animal. Results displayed are means±SEM of each group. Each group contained 6 mice.

FIG. 6 illustrates the therapy of s.c. F9 tumors with different amounts of L19-GM-CSF. Daily i.v. injections for four consecutive days (arrows) with 60 μg of L19-GM-CSF demonstrated significant tumor growth retardation compared to saline (PBS) treated group.

EXAMPLES

Example 1

Preparation of Fusion Proteins

The cytokines were genetically fused to either the C- or the N-terminus of the scFv antibody fragments separated by a 15 amino acid linker. The resulting fragments, preceded by a secretion sequence required for secretion of recombinant proteins, were cloned in a mammalian expression vector and the fusion proteins were expressed in stably transfected HEK 293 cells. The constructs were purified from the culture medium by affinity chromatography on antigen columns at yields of 1-2 mg/l. Quality control was performed by SDS-PAGE and gelfiltration.

Example 2

Formulation and Administration of Fusion Proteins

Fusion proteins are solved in physiological solutions and administered intravenously to animals. The proteins are stored in one of the following buffers depending on their isoelectric point and the desired storage time. Proteins are kept for long time storage (over one month) at minus 80° C. To prevent aggregation by repeated thaw and freeze cycles 1% Glycerol and 0.04% Tween 80 may be added.

PBS (Phosphate buffered saline): 100 mM NaCl, 30 mM $Na_2HPO_4 \times 2\ H_2O$, 20 mM $NaH_2PO_4 \times 2\ H_2O$, pH 7.4

K-PBS: 137 mM NaCl, 8 mM $Na_2HPO_4 \times 2\ H_2O$, 2.7 mM KCl, 1.5 mM $KH_2PO_4$, pH 7.4

PBS Siena: 20 mM NaCl, 6.7 mM $Na_2HPO_4 \times 2\ H_2O$, 1.8 mM KCl, 133 mM Mannitol, pH 6.3

TBS (Tris buffered saline): 20 mM Tris, 130 mM NaCl, pH 8.2

Injections are typically administered 3-5 times, daily or every second day. The dosage is selected according to literature values following routine experimentation.

Example 3

Targeting Efficacy of the Fusion Protein in 129Sv Mice Grafted with Subcutaneous F9 Tumors The in vivo targeting properties of a radioiodinated preparation of L19-IL10 were evaluated in a biodistribution experiment in 129SvEv mice carrying subcutaneous F9 teratocarcinomas Favorable tumor/organ ratios (ranging between 7:1 and 128:1) were observed 24 hours after intravenous administration. The in vivo targeting properties of radioiodinated preparations of L19-IL15, IL15-L19, IL24-L19 and L19-GM-CSF were evaluated in a biodistribution experiment in 129SvEv mice carrying subcutaneous F9 teratocarcinomas. Favorable tumor:organ ratios were observed 24 hours after intravenous administration.

Example 4

The Human Monoclonal Antibodies L19 and G11 Selectively Accumulate at Sites of Arthritis The in vivo targeting performance of L19 and G11 in mini-antibody format (Borsi et al., Int. J. Cancer, 102(1): 79-85 (2002)) was studied in arthritic mice using both fluorescence and radioactivity for antibody detection.

Figure 1:
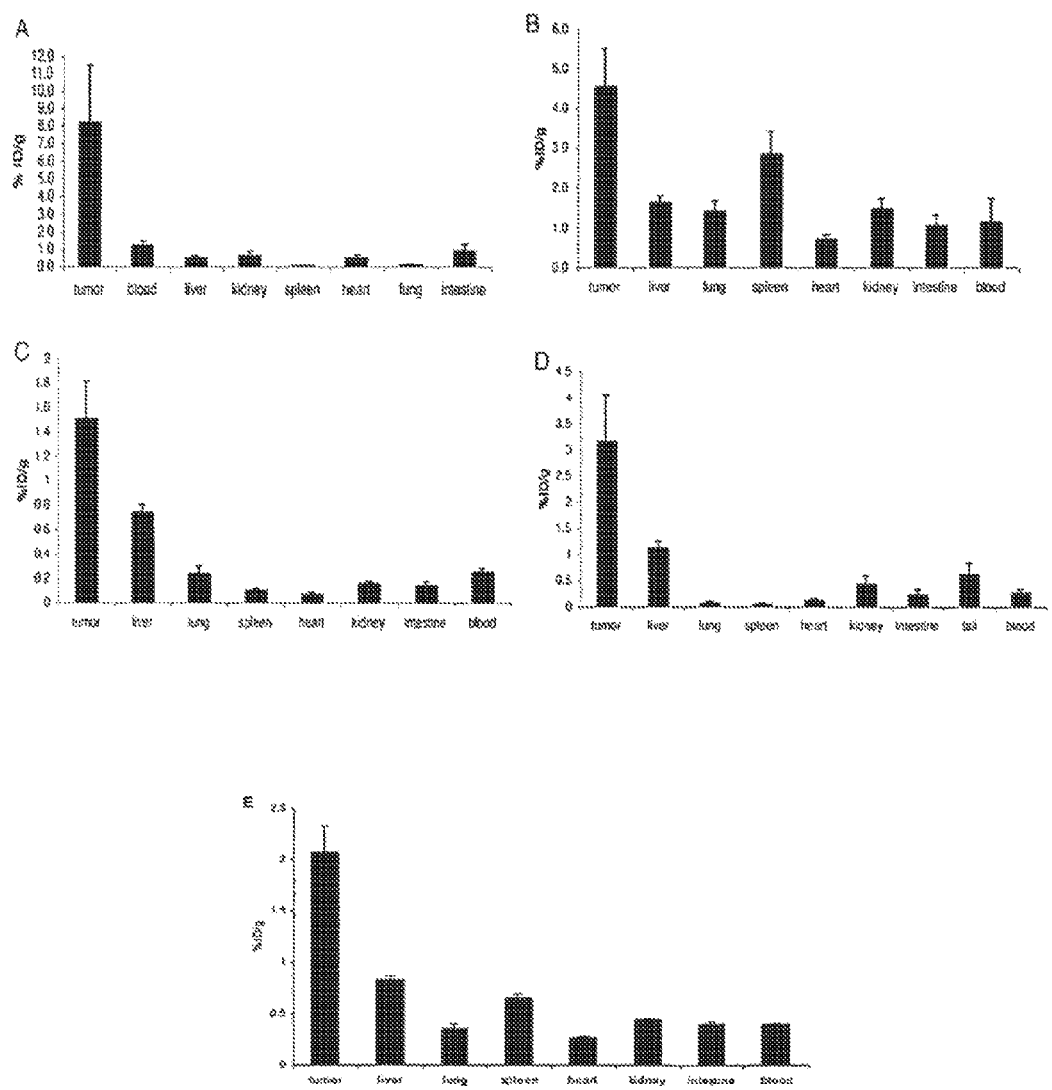
Figure 2:
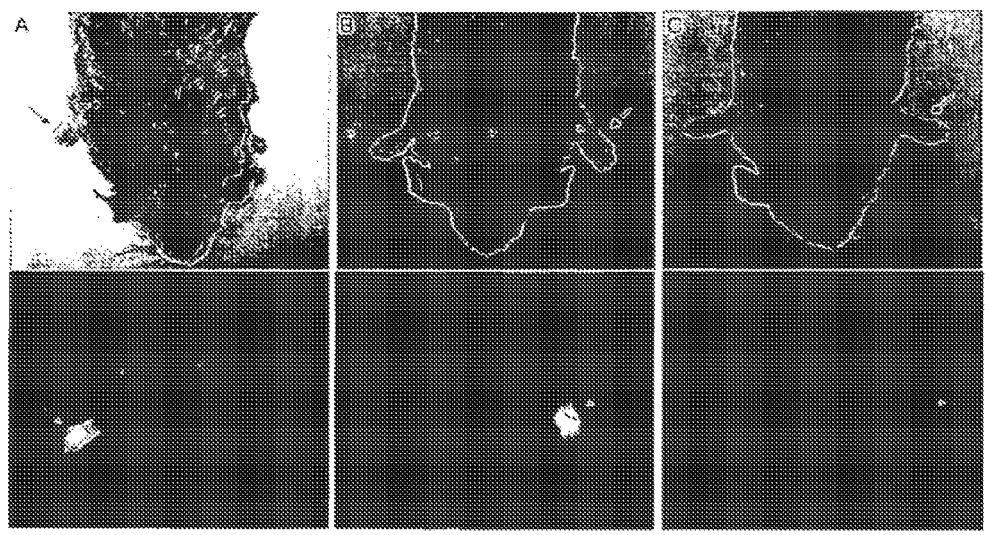

Arthritic mice were injected with SIP(L19), SIP(G11) or control SIP labelled with the near-infrared dye Alexa 750. Twenty-four hours after intravenous injection animals were imaged using an infrared fluorescence imager, revealing a strong and selective antibody accumulation in the lesions present in the arthritic limb in the case of SIP(L19) and SIP(G11) [FIG. 2]. By contrast, mice injected with control SIP, an antibody of irrelevant specificity in the mouse which was used as negative control, displayed only a faint fluorescence signal, due to non-specific extravasation of the labelled antibody through the leaky vessels in the inflamed extremity.

Figure 3:
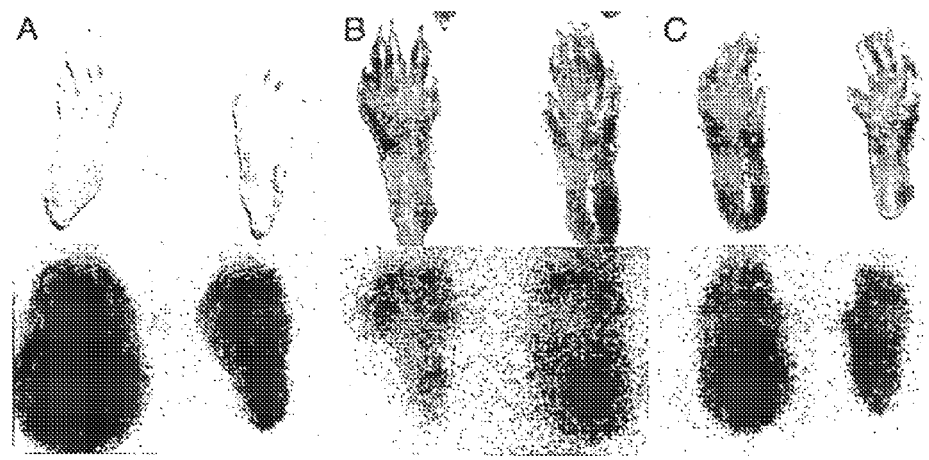

Arthritic mice were injected with radioactively labelled SIP(L19) and SIP(G11). After 24 h mice were sacrificed and paws imaged by autoradiography. A preferential accumulation of radioactivity was observed in the inflamed extremities of mice injected with SIP(L19) and SIP(G11), whereas no preferential antibody accumulation could be detected in mice exhibiting comparable grades of inflammation which had been injected with SIP antibody of irrelevant specificity in the mouse [FIG. 3].

Example 5

Therapeutic Efficacy of the Fusion Protein L19-IL10 in the Collagen-Induced Mouse Model of Arthritis The widest used and best known animal model for rheumatoid arthritis is the type II collagen induced arthritis (CIA) in either mouse or rat [Bliven et al., Arthritis Rheum. 29(9): 1131-8 ((1986)]. This model has been reported to have a number of characteristics in common with rheumatoid arthritis (RA) in humans, including humoral and cellular immunologic responses to collagen, linkage to genes residing in the major histocompatibility locus and some similar histologic manifestations. Maini and Feldmann have performed most of their pioneering work, such as the investigation of anti-tumor necrosis factor antibodies as a therapeutic strategy for RA, using this animal model [Williams et al., Proc. Natl. Acad. Sci. USA, 89(20): 9784-8 (1992); Williams et al., J. Immunol. 165(12): 7240-5 (2000)].

Effect of Targeted Delivery of Cytokines to Arthritic Lesions:

In a first experiment, the therapeutic potential of L19-IL10 was compared to that of L19-IL2 and L19-TNF using mice with CIA. Saline-injected mice were used as a control group. Mice received three injections every 48 h starting on day 1 after onset of arthritis. The cumulative doses, which were equal to the ones previously used for tumor therapy experiments, were 60 µg of L19-IL2 and 15 µg of L19-TNF. 450 µg of L19-IL10 per mouse were used in this experiment and in subsequent experiments with antibody-IL10 fusion proteins, in line with IL10 doses previously found to be active and not toxic in mice.

Figure 4:
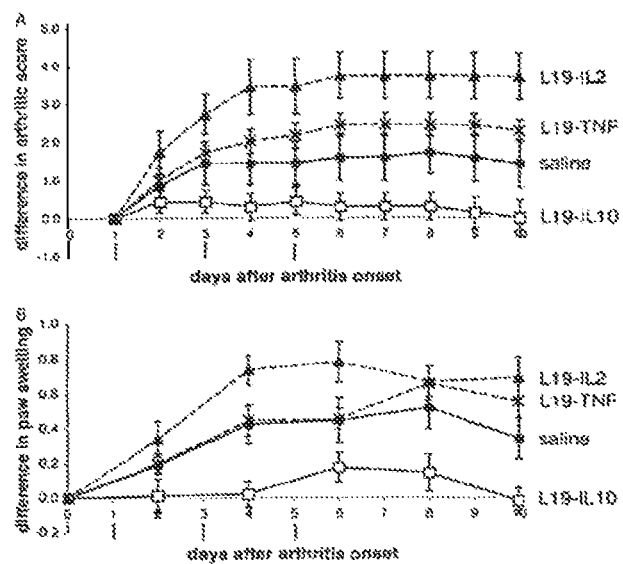

L19-IL10 had a clear therapeutic effect on arthritic score and on paw swelling (see FIG. 4). The magnitude of this effect was comparable to that observed for TNF-neutralizing antibodies in the same animal model. By contrast, L19-IL2 and L19-TNF led to a rapid and pronounced swelling of the affected limbs, which was more severe than in the saline control group. None of the treated animals died or exhibited a weight loss of more than 15% and arthritic parameters did not significantly worsen after the third antibody administration (FIG. 4).

Figure 5:
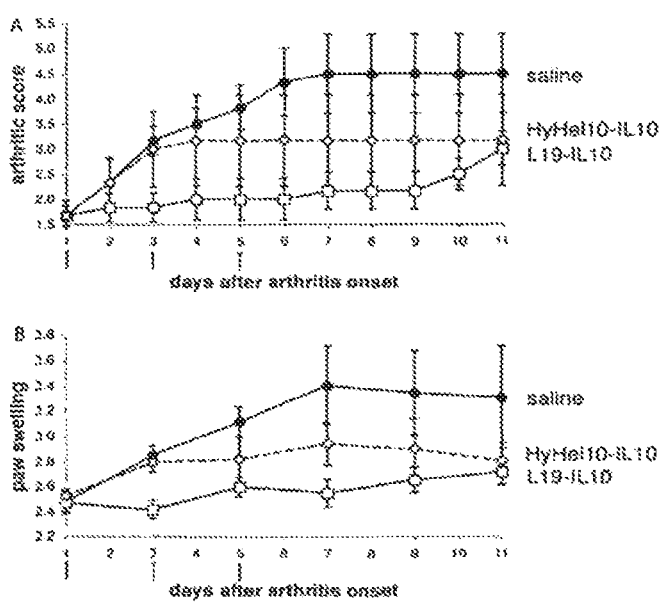

Comparison of Targeted Delivery Compared with Systemic Application of IL10:

In order to demonstrate a therapeutic advantage of a targeted version of IL10, when compared to the untargeted cytokine, the two fusion proteins L19-IL10 and HyHel10-IL10 were investigated in the CIA model of arthritis. As in the previous experiment groups of 6 arthritic mice were treated with three injections of L19-IL10, HyHel10-IL10 or saline every second day starting on the first day of arthritis onset. For both fusion proteins the cumulative dose administered to each mouse was 450 µg. As expected, L19-IL10 demonstrated a significant therapeutic response when compared to the saline control group, with arthritic score and paw swelling remaining low until day 9 after arthritis onset (i.e., 4 days after the last injection). Consistent with previous observations of a therapeutic activity of IL10 in this model the non-targeted HyHEL10-IL10 fusion protein displayed a therapeutic benefit compared to the saline control, which was, however, not as efficient as in the case of L19-IL10 (FIG. 5).

Example 6

Figure 6:
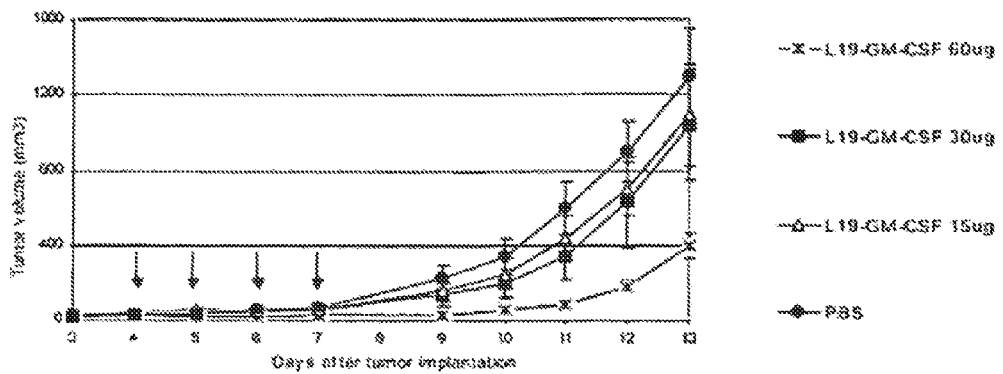
Figure 7:
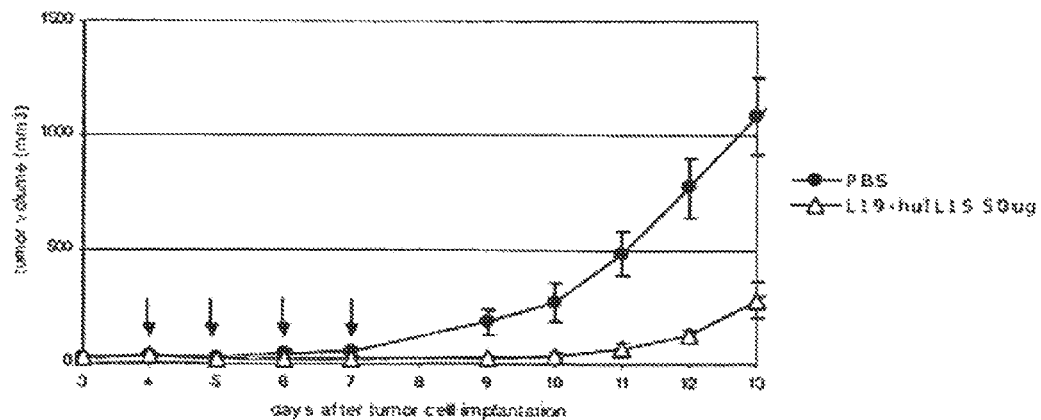
FIG. 7 illustrates the therapy of s.c F9 tumors with L19-IL15. Daily i.v. injections for four consecutive days (arrows) with 50 μg L19-IL15 demonstrated significant tumor growth retardation compared to control (PBS) group.
Figure 8:
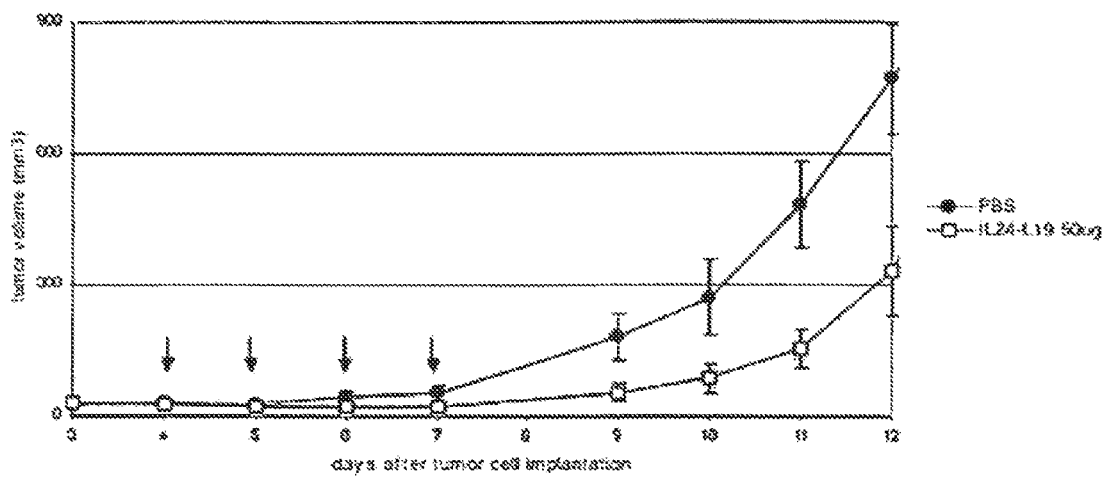
FIG. 8 illustrates the therapy of s.c F9 tumors with IL24-L19. Daily i.v. injections for four consecutive days (arrows) with 50 μg IL24-L19 showed significant tumor growth retardation compared to control (PBS) group.

Therapeutic Efficacy of the Fusion Proteins L19-IL15, IL24-L19 and L19-Gm-CSF in 129Sv Mice Grafted with Subcutaneous F9 Tumors In a first experiment, the therapeutic potential of L19-GM-CSF, L19-IL15 and IL24-L19 was evaluated using mice with s.c. F9 tumors. Saline-injected mice were used as a control group. Mice received a total of four injections every 24 h starting on day 4 after tumor cell implantation when tumors were already visible and measurable. The cumulative doses which were equal to the ones previously used for tumor therapy experiments were 240 μg for L19-GM-CSF, 200 μg for L19-IL15 and 200 μg for IL24-L19. All three fusion proteins were non-toxic in this setting and demonstrated significant tumor growth retardation compared to the control group (FIGS. 6-8).

---

The invention claimed is:

1. A fusion protein comprising:
   (i) an antibody, functional fragment or functional derivative thereof having specific binding affinity to the extracellular domain B of oncofetal fibronectin (ED-B) fused to
   (ii) an IL-10 cytokine.

2. The fusion protein of claim 1, wherein the antibody, functional fragment or functional derivative thereof is selected from the group consisting of polyclonal antibodies, monoclonal antibodies, chimeric antibodies, humanized antibodies, CDR-grafted antibodies, Fv-fragments, Fab-fragments, Fab$_2$-fragments and antibody-like binding proteins.

3. The fusion protein according to claim 1, wherein the functional derivative of the antibody is the diabody L19 (short) having the amino sequence set forth in SEQ ID NO: 7.

4. The fusion protein according to claim 1, wherein a member of the group consisting of L19 (long) and L19 (short), is fused to an IL-10 cytokine.

5. The fusion protein according to claim 1, wherein the IL-10 cytokine is a murine IL-10 cytokine or a human IL-10 cytokine.

6. The fusion protein according to claim 1, wherein the IL-10 cytokine is fused N-terminally or C-terminally to the antibody, functional fragment or functional derivative thereof.

7. The fusion protein according to claim 1, wherein the antibody fragment or functional derivative thereof is L19.

8. The fusion protein according to claim 1, which is L19-IL-10.

9. The fusion protein according to claim 1, having the amino acid sequence set forth in SEQ ID NO: 14.

10. A method for manufacturing a medicament, comprising:
    preparing a pharmaceutical composition comprising:
      a therapeutically effective amount of a fusion protein according to claim 1, and
      at least one pharmaceutically acceptable excipient selected from carriers, stabilizers, antioxidants, pH-regulating substances and controlled-release excipients;
    wherein the medicament is for treating rheumatoid arthritis.

11. A pharmaceutical composition comprising at least one fusion protein according to claim 1 and optionally a pharmaceutically acceptable excipient.

12. A method of treating rheumatoid arthritis, comprising: administering an effective amount of the pharmaceutical composition according to claim 11 to a patient in need thereof.

* * * * *